United States Patent
Singh et al.

(10) Patent No.: US 6,778,268 B1
(45) Date of Patent: Aug. 17, 2004

(54) SYSTEM AND METHOD FOR PROCESS MONITORING OF POLYSILICON ETCH

(75) Inventors: Bhanwar Singh, Morgan Hill, CA (US); Bharath Rangarajan, Santa Clara, CA (US); Michael K. Templeton, Atherton, CA (US)

(73) Assignee: Advanced Micro Devices, Sinc., Sunnyvale, CA (US)

( * ) Notice: Subject to any disclaimer, the term of this patent is extended or adjusted under 35 U.S.C. 154(b) by 129 days.

(21) Appl. No.: 09/973,231

(22) Filed: Oct. 9, 2001

(51) Int. Cl.[7] ............... G01N 21/55; G01N 21/00; C23F 1/00; G01V 3/12; G03F 9/00
(52) U.S. Cl. ............... 356/237.5; 356/448; 156/345.25; 324/337; 430/5; 430/30
(58) Field of Search ............... 356/445, 448, 356/237.2, 237.5; 156/345.24, 345.25; 324/323, 332, 337; 430/5, 30

(56) References Cited

U.S. PATENT DOCUMENTS

| | | | | |
|---|---|---|---|---|
| 4,710,642 A | * | 12/1987 | McNeil | 250/559.04 |
| 5,164,790 A | * | 11/1992 | McNeil et al. | 356/496 |
| 5,889,593 A | * | 3/1999 | Bareket | 356/445 |
| 6,259,521 B1 | * | 7/2001 | Miller et al. | 356/237.5 |
| 6,265,273 B1 | * | 7/2001 | Avanzino et al. | 438/304 |
| 6,270,622 B1 | * | 8/2001 | Klippert et al. | 156/345.12 |
| 6,337,262 B1 | * | 1/2002 | Pradeep et al. | 438/574 |
| 6,545,753 B2 | * | 4/2003 | Subramanian et al. | 356/237.5 |
| 6,562,248 B1 | * | 5/2003 | Subramanian et al. | 216/12 |
| 6,577,384 B2 | * | 6/2003 | Wei et al. | 356/73 |
| 2003/0153104 A1 | * | 8/2003 | Rangarajan et al. | 438/14 |

* cited by examiner

*Primary Examiner*—Russell Adams
*Assistant Examiner*—Magda Cruz
(74) *Attorney, Agent, or Firm*—Amin & Turocy, LLP

(57) ABSTRACT

An in-line system and method for determining T-top gate dimensions is provided. The system comprises a wafer structure undergoing a T-top gate formation process; a scatterometry system coupled to the formation process for directing light at and collecting reflected light from the wafer structure; a signature store; a T-top gate formation analysis system coupled to the scatterometry system and to the signature store for determining the T-top gate dimensions; and a feedback control system coupled to the T-top gate formation analysis system for optimizing T-top gate formation. The method comprises providing a wafer structure having a T-top gate formed thereon; generating a signature associated with the T-top gate; comparing the generated signature with a signature store to determine the dimensions of the T-top gate; if the dimensions of the T-top gate are not within a pre-determined acceptable range, then adjusting T-top gate process parameters using feedback control.

34 Claims, 23 Drawing Sheets

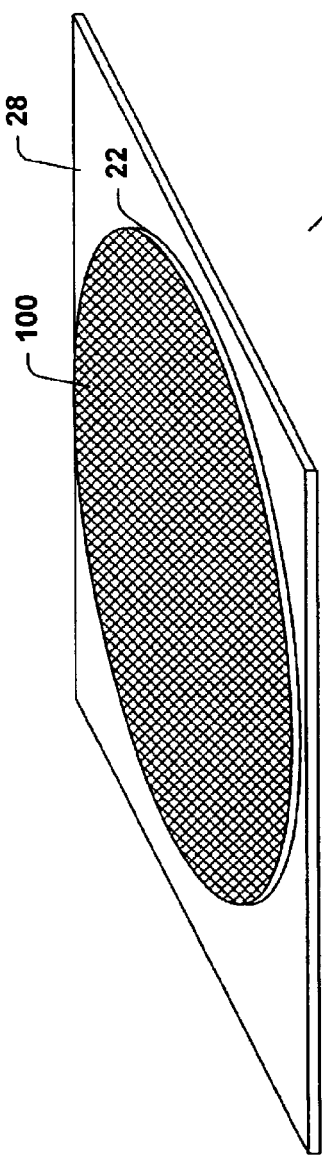
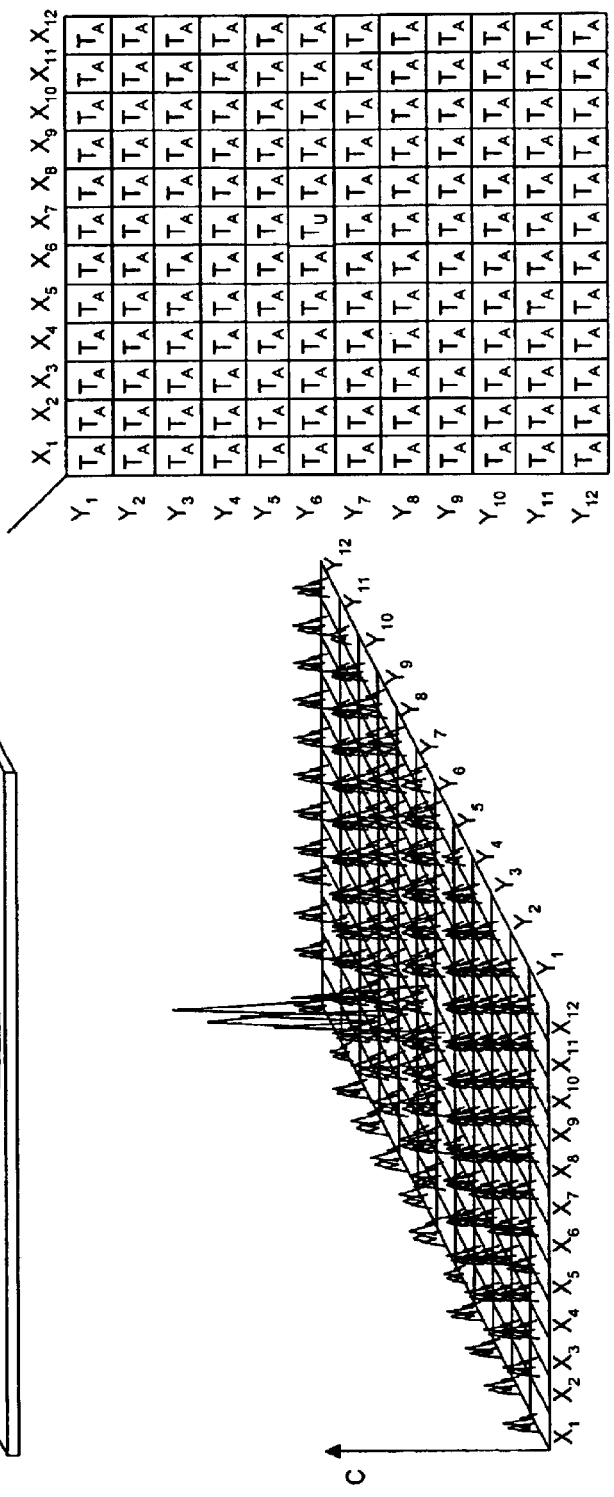
Fig. 15
Fig. 17
Fig. 16

SYSTEM AND METHOD FOR PROCESS MONITORING OF POLYSILICON ETCH

TECHNICAL FIELD

The present invention relates generally to semiconductor processing, and in particular to a system and method for monitoring and regulating the formation of a T-top polysilicon etch (T-top gate structure).

BACKGROUND

Historically, gate structures with a base area width smaller than a gate contact area (e.g., T-gate and Y-gate structures) have been advantageous to several technologies. For example, MESFET and HEMT (variant of gallium arsenide field effect transistor technology), which are utilized in satellite broadcasting receivers, high-speed logic circuits and power modules, have employed T-gate and/or Y-gate structures. Such devices are employed in field effect transistors to facilitate ultra-high frequency range operation. Employing a gate structure with a shorter gate length reduces the gate channel, with resulting speed increases and power consumption reductions. Such gate structures similarly provide reductions to the parasitic resistances and capacitances that limit device speed. A shorter gate length decreases transmit time for carriers in the channel but also increases series resistance of the gate electrode itself, slowing down the device and degrading the frequency characteristics of the device. Providing a gate structure with a smaller base than its contact area decreases the gate channel while providing a low gate series resistance due to the wider contact area. Decreasing the gate channel while lowering the gate series resistance improves device drive current capability and performance. Thus, providing gates with such features is desired in semiconductor manufacturing. But conventional techniques for fabricating such gates suffer from shortcomings.

In the semiconductor industry, there is a continuing trend toward higher device densities. To achieve these higher densities there have been, and continue to be, efforts toward scaling down device dimensions (e.g., at sub-micron levels) on semiconductor wafers. In order to accomplish such high device packing densities, smaller and smaller features sizes fabricated with more precise patterns are required. This may include the profile of the feature being formed (e.g., T-gate, Y-gate), the slope of a feature face, the depth of a trench being etched, and the surface geometry, such as corners, angles and edges of various features. The requirement of small features with complicated profiles and close spacing between adjacent features requires high-resolution photolithographic processes.

In general, lithography refers to processes for pattern transfer between various media. Lithography is a technique used for integrated circuit fabrication in which a silicon slice, the wafer, is coated uniformly with a radiation-sensitive film, (the resist), and an exposing source (such as optical light, x-rays, or an electron beam) illuminates selected areas of the surface through an intervening master template, (the mask), for a particular pattern. The lithographic coating is generally a radiation-sensitive coating suitable for receiving a projected image of the subject pattern. Once the image is projected, it is indelibly formed in the coating. The projected image may be either a negative or a positive of the subject pattern. Exposure of the coating through a photomask causes the image area to become either more or less soluble, depending on the coating, in a particular solvent developer. The more soluble areas are removed in the developing process to leave the pattern image in the coating as less soluble polymer, which can subsequently be etched away.

Fabricating T-gate structures can require sophisticated etching. Conventionally, such etching has either not been feedback controlled, requiring precalculated etching properties and/or layer specific etching processes or has had feedback based on indirect information (e.g., amount of gas generated by plasma gas discharge etching). Such predetermined calculations and/or indirect feedback control may not provide fine enough control for etching processes required for forming T-gate structures. Removing insufficient amounts of the oxide layer and/or removing undesired portions of the oxide layer may result in features that are too large and/or exhibit undesired profiles. Similarly, removing too much of the oxide layer and/or removing undesired portions of the oxide layer may result in features that are too small and/or exhibit undesired profiles.

Recent advances in CMOS transistor architecture employ T-gate or Y-gate structures where the polysilicon gate electrode is narrowed in the gate regions and widened on top of the gate. However, conventional methods for forming a gate structure with a contact region wider than its base suffer from shortcomings. For example, the etch process that narrows the base of the structure is known to be difficult to control, especially with local pattern density. This can lead to variations in the gate width and asymmetric, undesired profiles. Conventional inspection systems such as scanning electron microscope (SEM) do not provide adequate information relating to the dimensions of the T-gate structures.

Due to the extremely fine patterns that are exposed on the photo resist, controlling the etching process, whereby oxide or other materials are removed, is a significant factor in achieving desired feature profiles. Thus, an efficient system, and/or method, to monitor T-top gate formation is desired to facilitate manufacturing ICs with desired feature profiles, which can increase the quality of the underlying wafer being manufactured.

SUMMARY

The following presents a simplified summary of the invention in order to provide a basic understanding of some aspects of the invention. This summary is not an extensive overview of the invention. It is not intended to identify key or critical elements of the invention or to delineate the scope of the invention. Its sole purpose is to present some concepts of the invention in a simplified form as a prelude to the more detailed description that is presented later.

One aspect of the present invention relates to a method for monitoring T-top gate formation. The method includes providing a wafer structure undergoing a T-top gate fabrication process; generating a signature associated with the wafer structure during a process step to monitor formation of the T-top gate; and comparing the generated signature to a signature store to determine a state of the T-top gate.

Another aspect of the present invention provides an in-line method for determining T-top gate dimensions comprising: providing a wafer structure having a T-top gate formed thereon; generating a signature associated with the T-top gate; comparing the generated signature with a signature store to determine the dimensions of the T-top gate; and if the dimensions of the T-top gate are not within a predetermined acceptable range, then adjusting T-top gate process parameters using feedback control.

Yet another aspect of the present invention provides An in-line method for determining T-top gate dimensions comprising: providing a wafer structure having a T-top gate formed thereon; directing an incident beam of light at the T-top gate; collecting the reflected light associated with the T-top gate; generating a signature associated with the T-top gate using the reflected light; comparing the generated signature with a signature store to determine the dimensions of the T-top gate; and if the dimensions of the T-top gate are not within a pre-determined acceptable range, then adjusting T-top gate process parameters using feedback control.

Still another aspect of the present invention relates to an in-line system for monitoring T-top gate formation. The system comprises a wafer structure undergoing a T-top gate formation process; a T-top gate formation monitoring system for generating a signature associated with wafer surface dimensions during a process step; and a signature store coupled to the monitoring system, wherein the generated signature is compared to the signature store to determine a state of the T-top gate.

Still another aspect of the present invention relates to An in-line system for determining T-top gate dimensions comprising: a wafer structure undergoing a T-top gate formation process; a scatterometry system coupled to the formation process for directing light at and collecting reflected light from the wafer structure; a signature store comprising known signatures associated with T-top gate formation; a T-top gate formation analysis system coupled to the scatterometry system and to the signature store for determining the T-top gate dimensions; and a feedback control system ret coupled to the T-top gate formation analysis system for optimizing T-top gate formation.

Yet another aspect of the present invention relates to an in-line system for determining T-top gate dimensions. The system comprises means for providing a wafer structure having a T-top gate formed thereon; means for generating a signature associated with the T-top gate; means for comparing the generated signature with a signature store to determine the dimensions of the T-top gate; and if the dimensions of the T-top gate are not within a pre-determined acceptable range, then means for adjusting T-top gate process parameters using feedback control.

To the accomplishment of the foregoing and related ends, certain illustrative aspects of the invention are described herein in connection with the following description and the annexed drawings. These aspects are indicative, however, of but a few of the various ways in which the principles of the invention may be employed and the present invention is intended to include all such aspects and their equivalents. Other advantages and novel features of the invention may become apparent from the following detailed description of the invention when considered in conjunction with the drawings.

BRIEF DESCRIPTION OF THE DRAWINGS

FIG. 15 is a perspective illustration of a wafer that may be aligned in accordance with an aspect of the present invention.

FIG. 16 is a representative three-dimensional grid map of a wafer illustrating overlay signature measurements taken at grid blocks of the grid map in accordance with an aspect of the present invention.

FIG. 17 is an overlay signature measurement table correlating the overlay measurements of FIG. 16 with desired values for the overlay measurements in accordance with the present invention.

DETAILED DESCRIPTION

Figure 1:
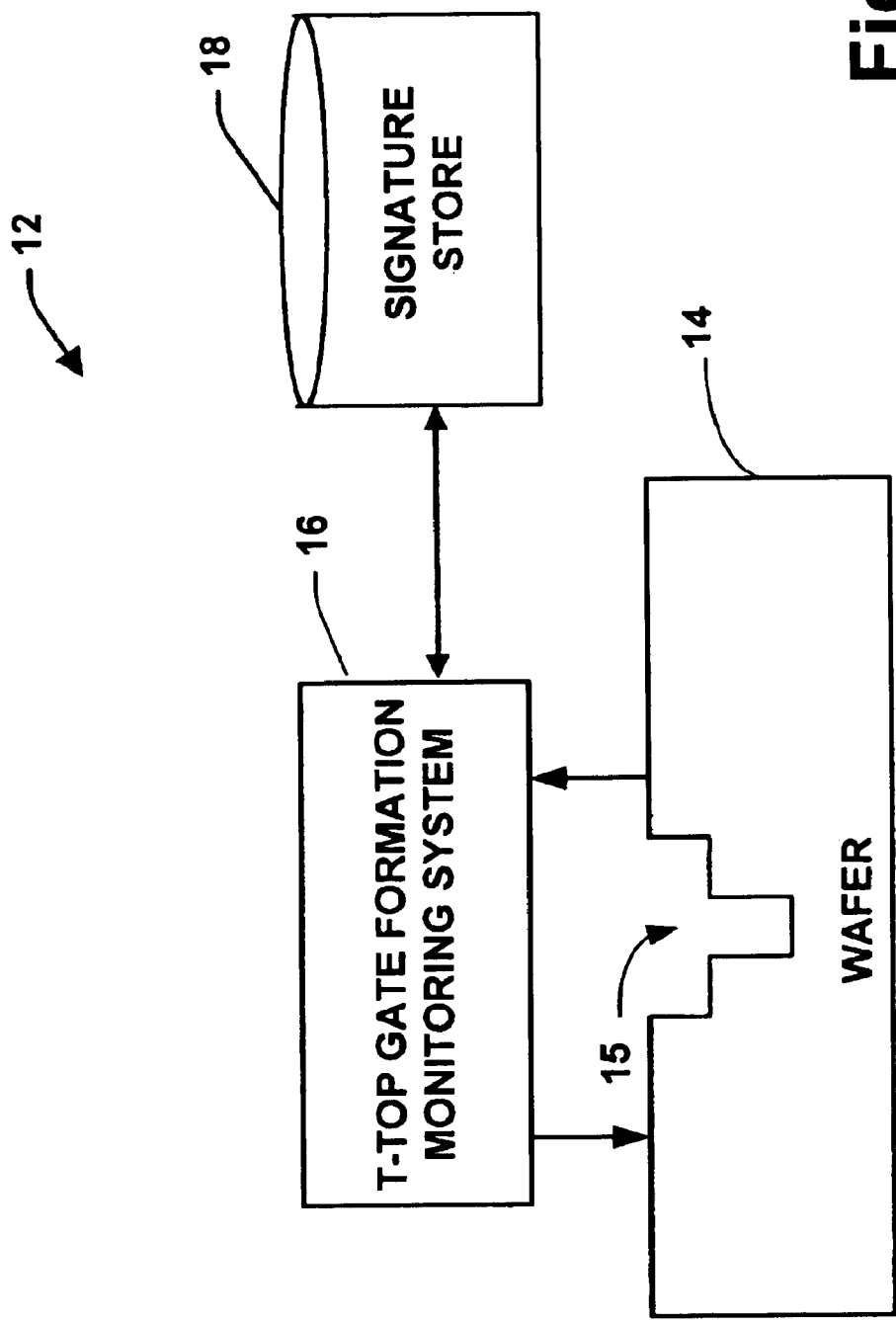
FIG. 1 is a high-level block diagram of a system to monitor t-top gate formation in accordance with an aspect of the present invention.

The present invention is now described with reference to the drawings, wherein like reference numerals are used to refer to like elements throughout. In the following description, for purposes of explanation, numerous specific details are set forth in order to provide a thorough understanding of the present invention. It may be evident, however, to one skilled in the art that the present invention may be practiced without these specific details. In other instances, well-known structures and devices are shown in block diagram form in order to facilitate description of the present invention.

It is to be appreciated that various aspects of the present invention may employ technologies associated with facilitating unconstrained optimization and/or minimization of error costs. Thus, non-linear training systems/methodologies (e.g., back propagation, Bayesian, fuzzy sets, non-linear regression, or other neural networking paradigms including mixture of experts, cerebella model arithmetic computer (CMACS), radial basis functions, directed search networks and function link networks) may be employed.

FIG. 1 illustrates a high level system 12 for monitoring T-top gate formation according to the present invention. The system 12 includes a T-top formation monitoring system 16 that monitors and analyzes a wafer 14 undergoing T-top gate formation (e.g., for T-top gate dimensions). The analysis system 16 employs a suitable tool (e.g., scatterometry system, ellipsometry system) to obtain a signature corresponding to the attributes of the wafer 14 being reviewed. The analysis system 16 obtains such signature and compares it to a database of historical overlay signatures stored in a signature store 18. The historical database of signatures provides for M number of profiles (M being an integer) relating to various T-top gate states. The monitoring system 16 looks for similarity between the current signature and at least one of the historical signatures. Based on such comparison and other extrinsic data (e.g., process parameters) as well as other analytical tools, the monitoring system 16 makes an inference as to the current state of the T-top gate (e.g., if T-top gate is forming correctly).

Figure 2:
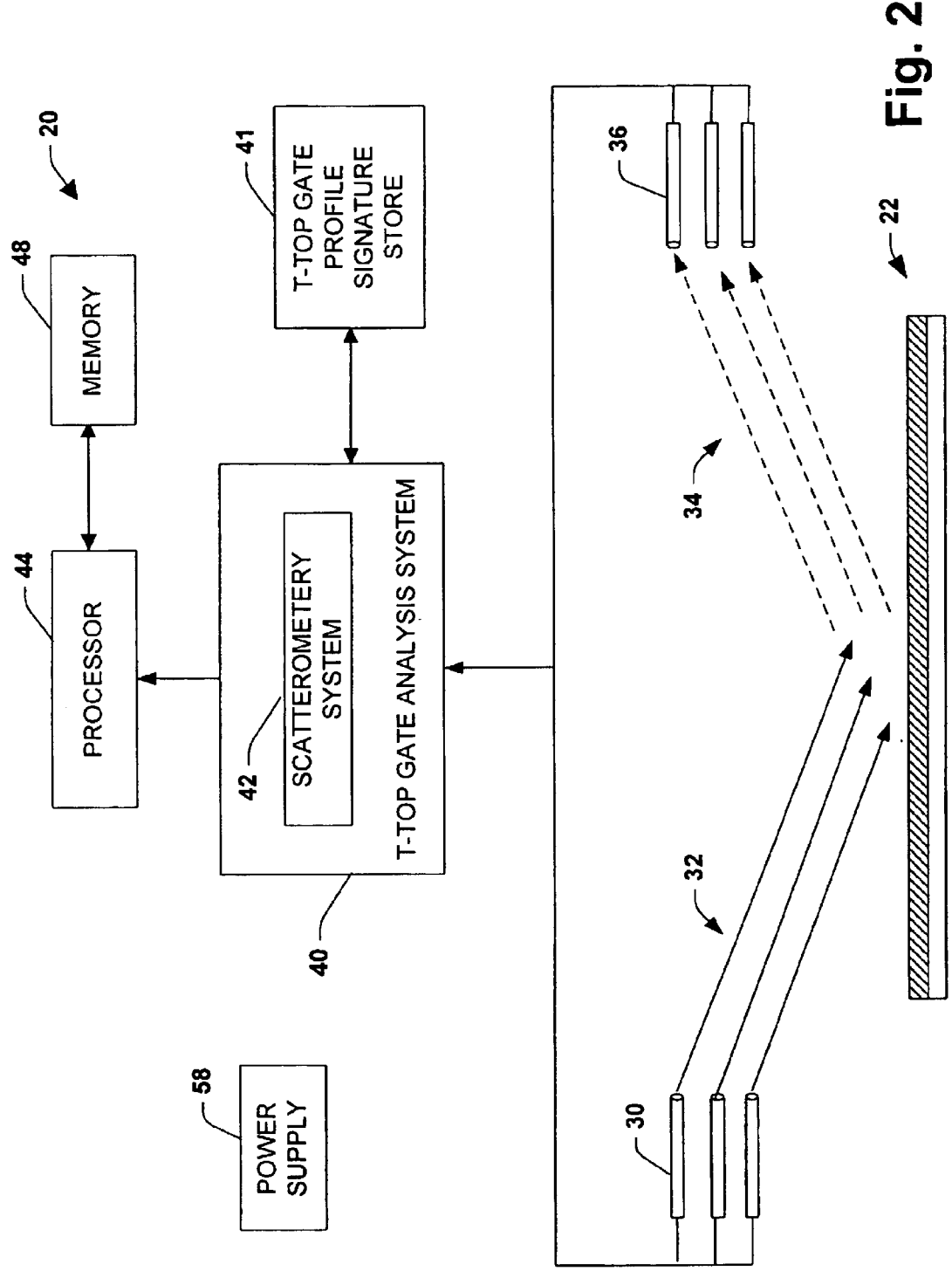
FIG. 2 is schematic block diagram of an in-line system to monitor t-top gate formation in accordance with an aspect of the present invention.

Referring now to FIG. 2, a schematic block diagram of an in-line system 20 for monitoring T-top gate formation is shown in accordance with one aspect of the present invention. A wafer 22 is shown in position for being monitored as it proceeds through a T-top gate fabrication process. The wafer 22, comprising of more than one layer, is supported by a suitable platform such as a chuck 28. A light source 30 directs an incident beam of light 32 at the wafer 22 in order to generate a signature of the wafer 22. The light source 30 may comprise of one or more or a series of light sources directed at the wafer 22. Examples of light sources contemplated by the present invention include, but are not limited to, a laser such as a laser diode or a helium neon gas laser.

Light reflected 34 from the wafer 22 is collected by a light detector 36. The reflected light 34 yields a signature associated with the wafer 22 as it undergoes the T-top gate formation process, which is used to determine T-top gate dimensions. The light detector 36 comprises one or more light detecting devices and collects light in accordance with conventional scatterometry techniques. Examples of light detectors include photo diodes and photo detectors. It should be appreciated that the incident light 32 may also pass through the wafer 22 and collected using the light detector 36 as previously described.

The reflected light 34 is communicated to a T-top gate analysis system 40, which is operatively coupled to the light detector 36. The T-top gate analysis system 40 generates a signature from the reflected light which corresponds to a profile of the wafer 22.

The T-top gate analysis system 40 comprises a conventional scatterometry system (FIGS. 6 and 7) and transforms the reflected light 34 into a signature using the scatterometry system and related scatterometry techniques. It is to be appreciated that any suitable scatterometry system may be employed to carry out the present invention, and such systems are intended to fall within the scope of the claims appended hereto. Sample scatterometry systems are briefly described in association with FIG. 18 and FIG. 19.

In addition, the T-top gate analysis system 40 may be coupled to any one of a plurality of processors 44, such as the AMD K7, and/or other similar and compatible processors. The manner in which the T-top gate analysis system 40 can be programmed to carry out the functions relating to the present invention will be readily apparent to those having ordinary skill in the art based on the description provided herein. The processor 44 may also comprise a memory 48 for retaining information generated and received by the analysis system 40.

The analysis system 40 determines T-top gate dimensions by comparing the generated signature associated with the wafer 22 to a T-top gate formation signature store 41. The signature store may include signatures corresponding to most typically encountered T-top gate formation profiles. The analysis system 40 may also generate cross-sectional, two-dimensional, and/or three-dimensional profiles of wafer 22.

Alternatively or in addition, the T-top gate analysis system 40 may communicate information relating to the T-top gate forming on the wafer 22 to the fabrication process system (not shown). Providing this information back to the fabrication system allows the system to optimize T-top gate formation. Wafers exhibiting unacceptable T-top gate formation, according to a pre-determined threshold level, may be marked or signaled for discard by the analysis system 40. The system 20 operates using any conventional power supply 58 suitable to carry out the present invention.

Turning now to FIGS. 3–14, a wafer 60 is shown undergoing a T-top gate formation process. The wafer 60 comprises a gate oxide layer 64 disposed over a silicon layer 62, a thin protection layer 66, a first sacrificial layer 68, a second sacrificial layer 70, and a photoresist layer 72 is formed on the second sacrificial layer 70. The fabrication process is monitored by the T-top gate monitoring system 40 in accordance with one aspect of the present invention. At substantially all times during the fabrication process, the wafer 60 is being monitored to determine dimensions of the T-top gate as it is being formed. Monitoring involves directing light 32 at the wafer 60 and collecting light reflected 34 from the wafer. The reflected light 34 is transformed or generated into a signature. The generated signature may then be compared to the signature store to determine the dimensions and the state of the T-top gate at that particular moment in the fabrication process.

Figure 3:
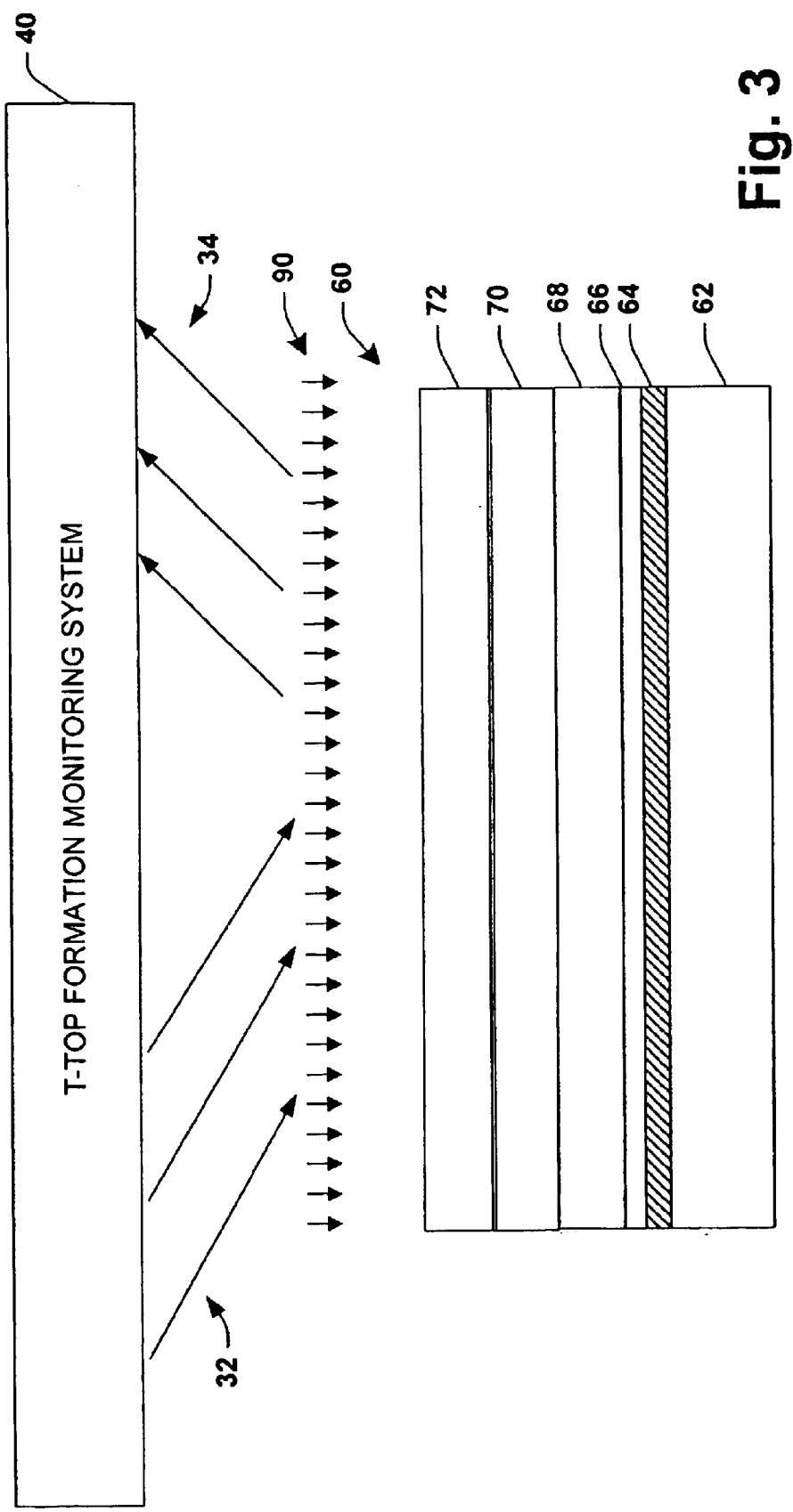
FIG. 3 is a schematic cross-sectional illustration of a wafer structure being etched in accordance with one aspect of the present invention.
Figure 4:
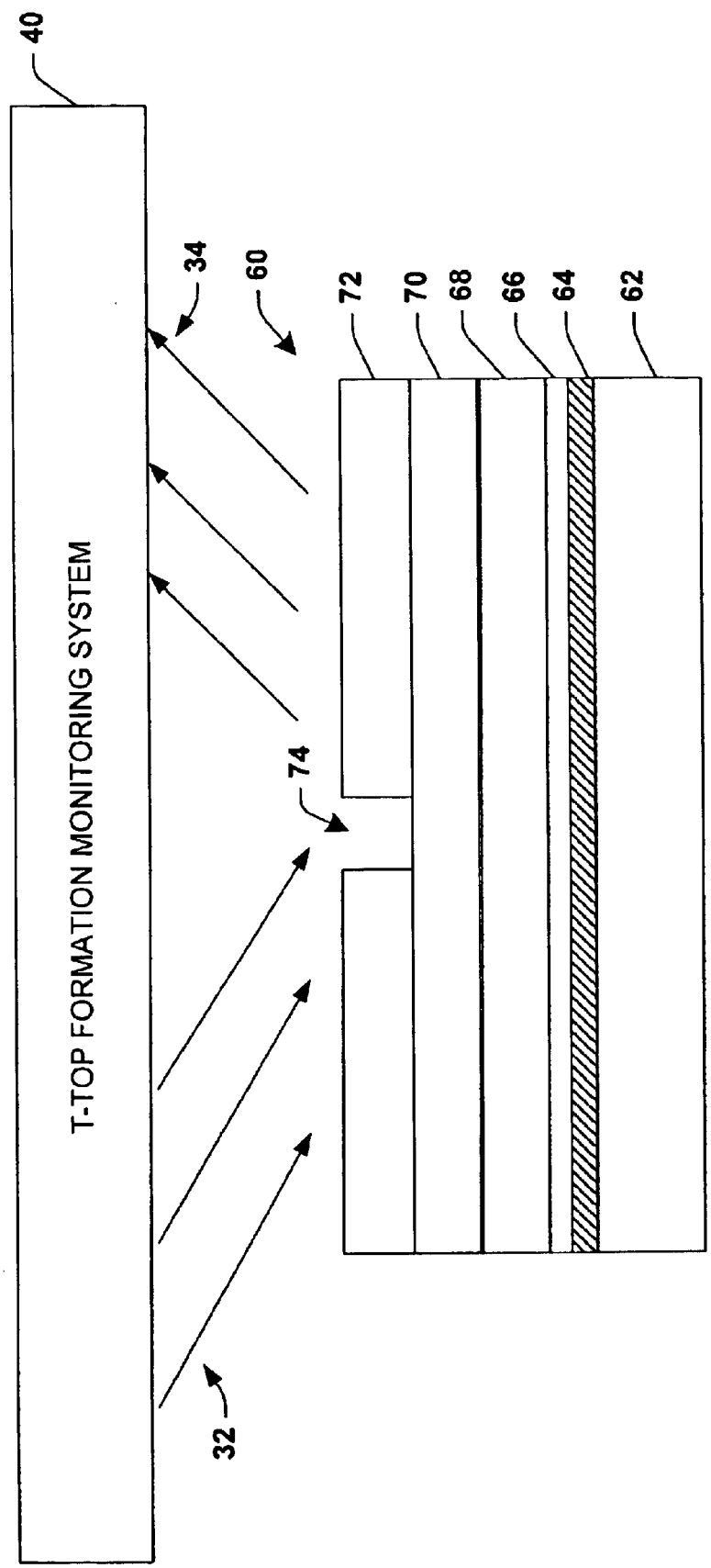
FIG. 4 is a schematic cross-sectional illustration of the structure of FIG. 3 after the photoresist layer has been etched in accordance with one aspect of the present invention.
Figure 5:
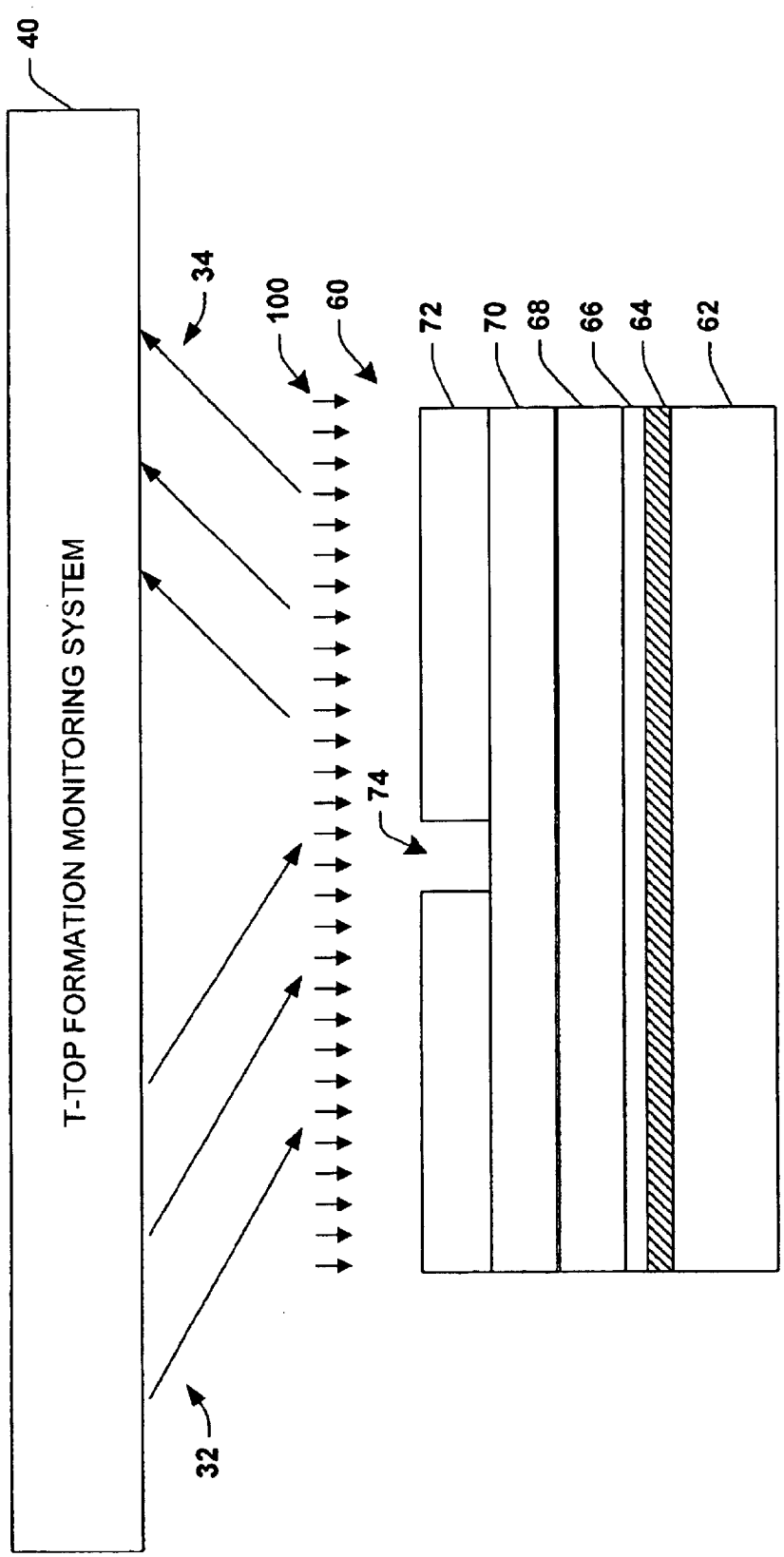
FIG. 5 is a schematic cross-sectional illustration of the structure of FIG. 4 being further etched in accordance with one aspect of the present invention.

In FIG. 3, an etching 90 (e.g., anisotropic reactive ion etching (RIE)) is performed to form an opening 74 in the photoresist layer 72 (FIG. 4). The photoresist layer 72 is patterned and is used as a mask for selectively etching the second sacrificial layer 70. Preferably, a selective etching is used to etch the material of the photoresist layer 72 at a relatively greater rate as compared to the rate that of the material of the second sacrificial layer 70. The photoresist layer 72 can be etched using a dark field mask employing a positive resist or in the alternative with a clear field mask with a negative resist to form the opening in the photoresist. Any suitable etching can be employed to etch the photoresist layer 72. For example, the photoresist layer 72 can be anisotropically etched with a plasma gas(es), herein carbon tetrafloride ($CF_4$) containing fluorine ions, in a commercially available etcher, such as a parallel plate RIE apparatus or, alternatively, an electron cyclotron resonance (ECR) plasma reactor. As discussed in association with FIGS. 1, 2 and 15–20, during the etching 90 the light 32 may be directed at the opening 74. Light reflecting from the opening 74 and/or one or more other layers, features and/or openings, for example, can be collected and analyzed to generate a signature associated with the opening 74. The generated signature can be compared to one or more stored signatures to determine whether to continue, adapt or stop the etching 90 which facilitates optimizing the T-top gate fabrication process.

Figure 6:
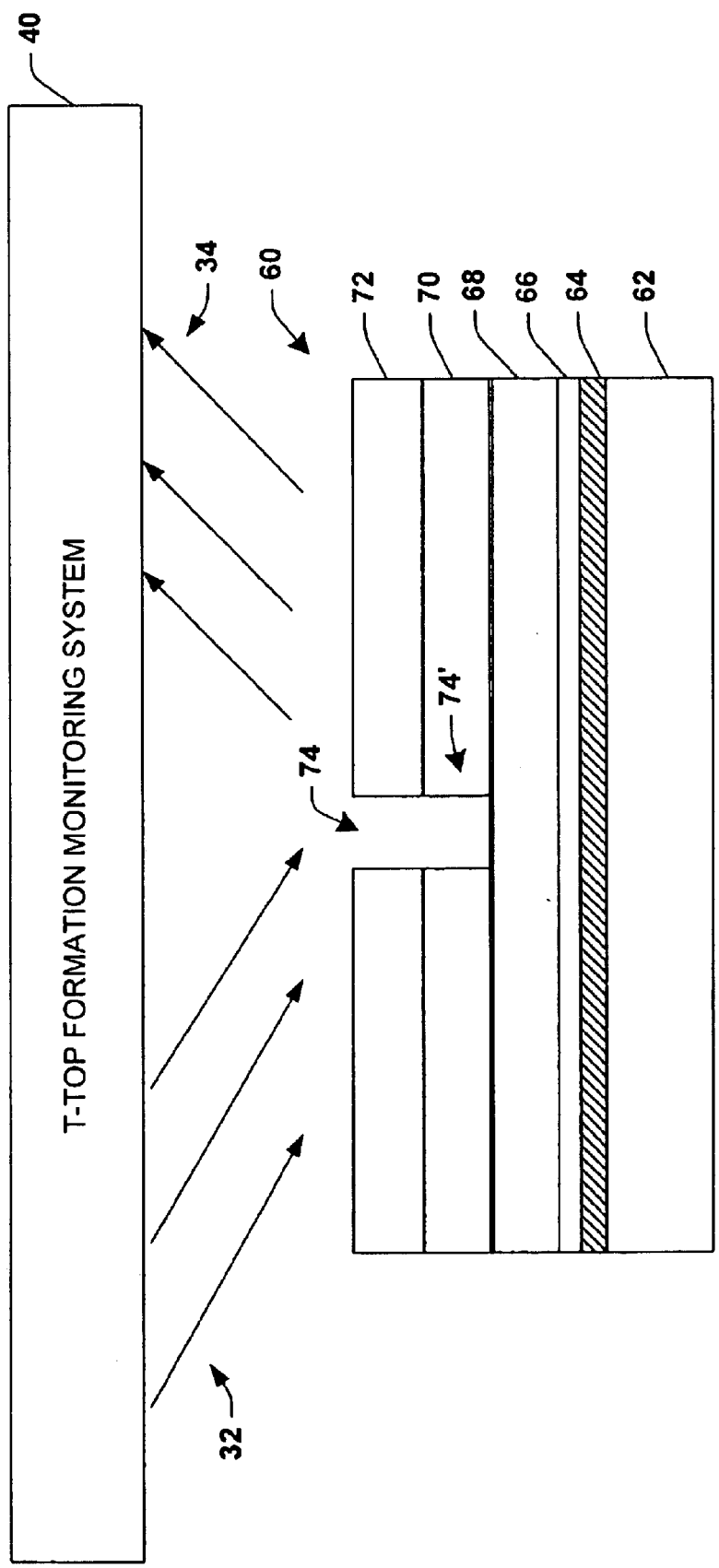
FIG. 6 is a schematic cross-sectional illustration of the structure of FIG. 5 after the second sacrificial layer has been etched in accordance with one aspect of the present invention.

An etching 100 (e.g., anisotropic reactive ion etching (RIE)) (FIG. 5) is performed to form an opening 74' in the second sacrificial layer 70 (FIG. 6). The photoresist layer is used as a mask for selectively etching the second sacrificial layer 70 to provide the opening 74' in the second sacrificial layer 70. Any suitable etching may be used to etch the second sacrificial layer 70. For example, the second sacrificial layer 72 can be anisotropically etched with a plasma gas(es), herein carbon tetrafloride ($CF_4$) containing fluorine ions, in a commercially available etcher, such as a parallel plate RIE apparatus or, alternatively, an electron cyclotron resonance (ECR) plasma reactor. Preferably, a selective etching is employed to etch the material of the second sacrificial layer 70 at a relatively greater rate as compared to the rate of the material of the patterned photoresist 72 and at a relatively greater rate as compared to the rate of the material of the underlying first sacrificial layer 68 to replicate the mask pattern of the photoresist layer 72 to thereby create the opening 74' in the second sacrificial layer 70. In an alternate aspect of the invention, the second sacrificial layer 70 and the first sacrificial layer 68 are formed from a single sacrificial layer. The single sacrificial layer is partially etched in the etching 100 from the top surface of the single sacrificial layer to a first depth, so that a portion of the single sacrificial layer remains below the first opening 74. As discussed in association with FIGS. 1 and 2, during the etching 100 a light may be directed at the opening 74'. Light reflecting from the opening 74' and/or one or more other layers, features and/or openings, for example, can be collected and analyzed to generate a signature associated with the opening 74'. The generated signature can be compared to one or more stored signatures to determine whether to continue, adapt or stop the etching 100.

Figure 7:
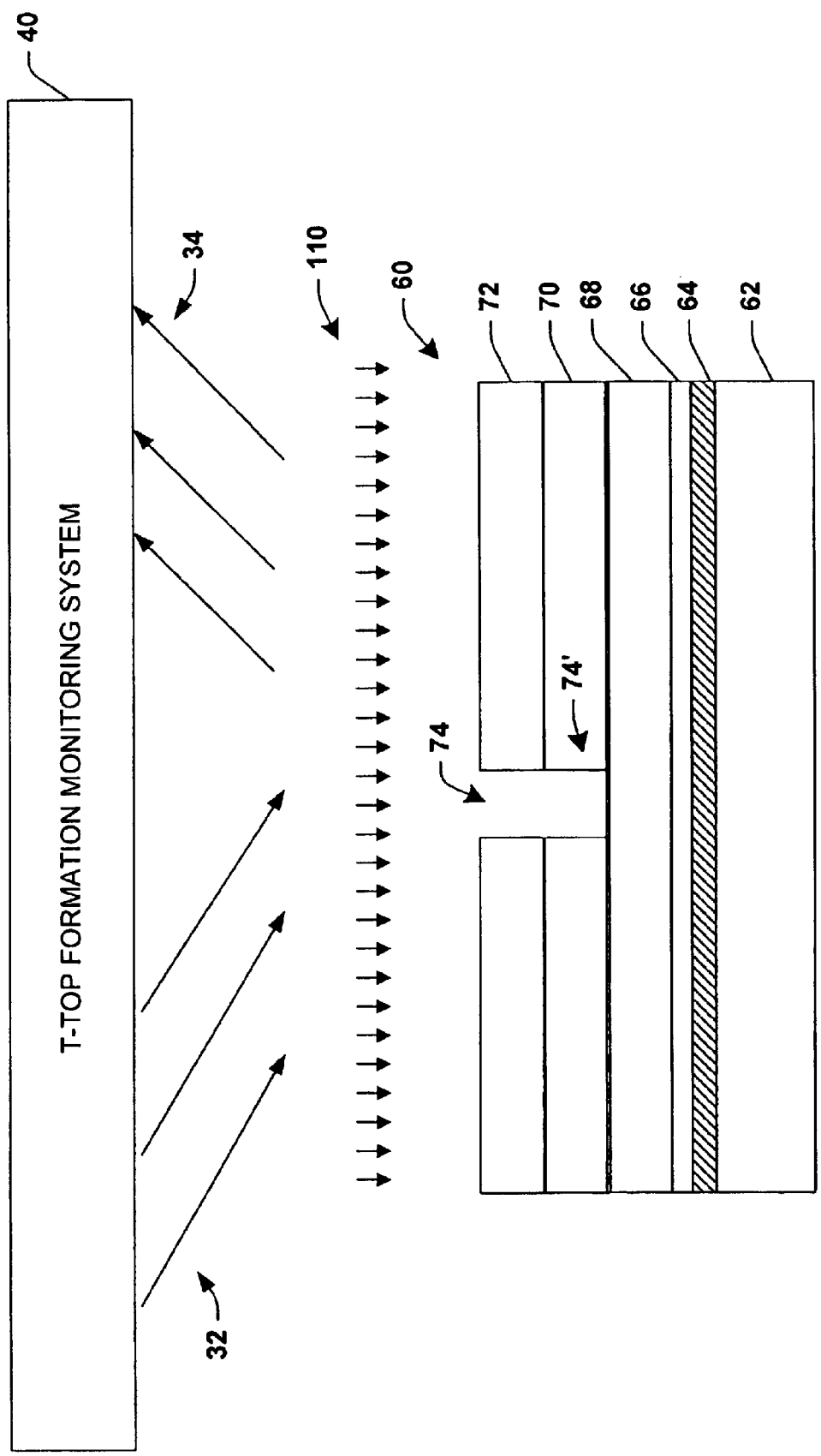
FIG. 7 is a schematic cross-sectional illustration of the structure of FIG. 6 undergoing yet further etching to expand the opening in the photoresist layer in accordance with one aspect of the present invention.
Figure 8:
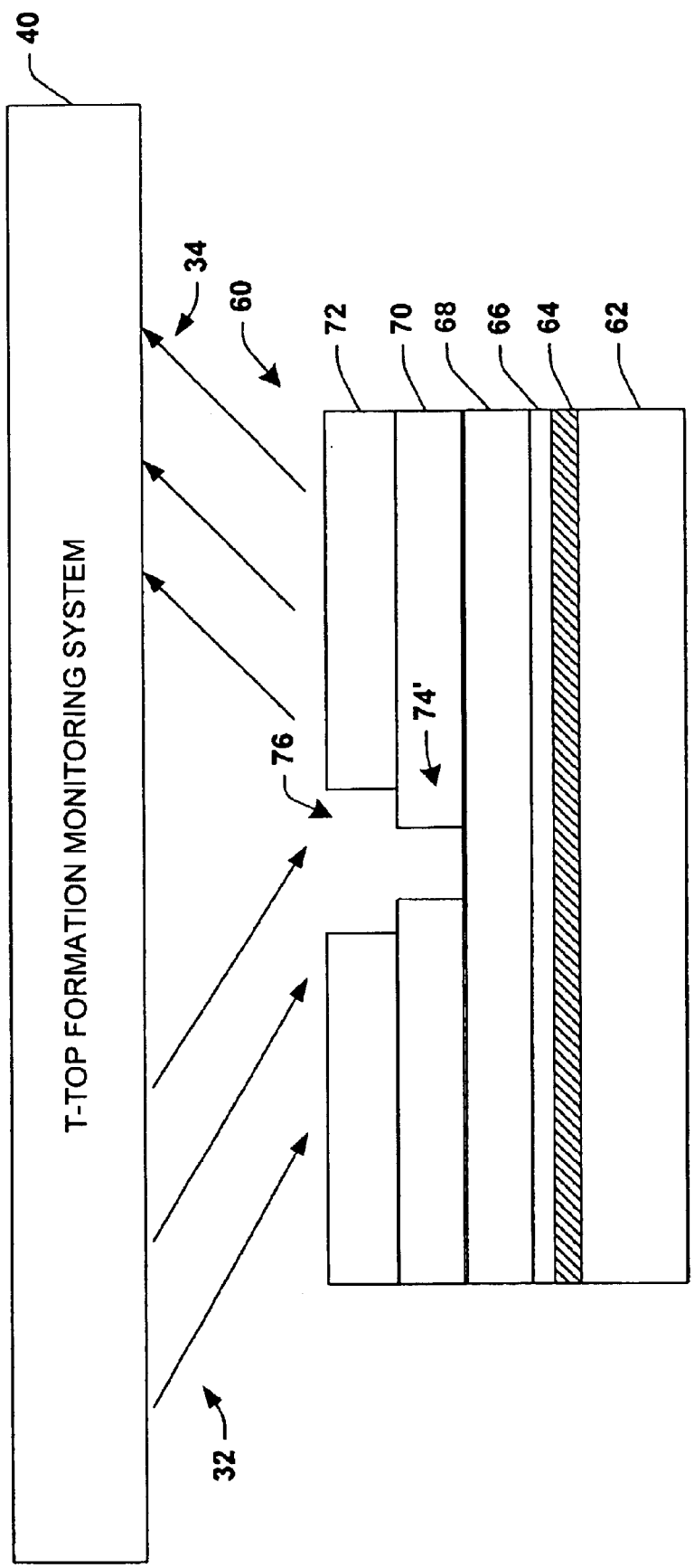
FIG. 8 is a schematic cross-sectional illustration of the structure of FIG. 7 after the opening in the photoresist layer has been expanded in accordance with one aspect of the present invention.
Figure 9:
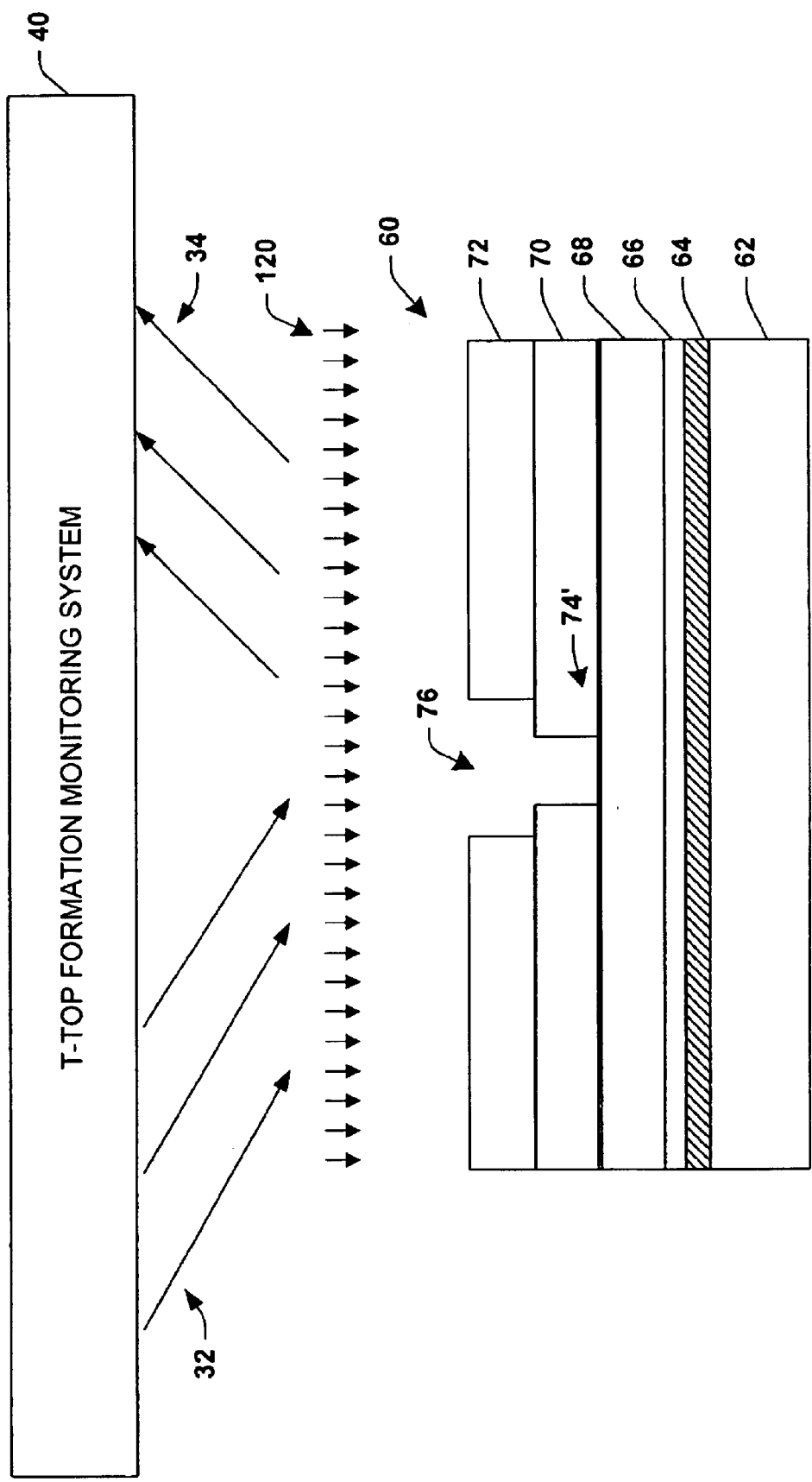
FIG. 9 is a schematic cross-sectional illustration of the structure of FIG. 8 undergoing further etching to expand the opening in the second sacrificial layer and to extend the opening through the first sacrificial layer in accordance with one aspect of the present invention.

FIG. 7 illustrates the structure 60 after the resist layer 72 undergoes a second resist etching 110 so that the resist opening 74 is expanded to form a larger opening 76 (FIG. 8), so that a portion of the top surface of the underlying second sacrificial layer 70 is exposed around the opening 74'. Preferably, the etching 110 is an oxygen plasma etch. If a single sacrificial layer is employed, the resist opening 74 is expanded to form a larger opening 76, so a portion of the top surface of the underlying single sacrificial layer is exposed around the opening 74'. As discussed in association with FIGS. 1 and 2, the incident light 32 may be directed at the opening 76 during the etching 110. Light reflecting 34 from the opening 76 and/or one or more other layers, features and/or openings, for example, can be collected and analyzed to generate a signature associated with the opening 76. The generated signature can be compared to one or more stored signatures to determine whether to continue, adapt or stop the etching 110, which facilitates optimizing T-top gate formation.

Figure 10:
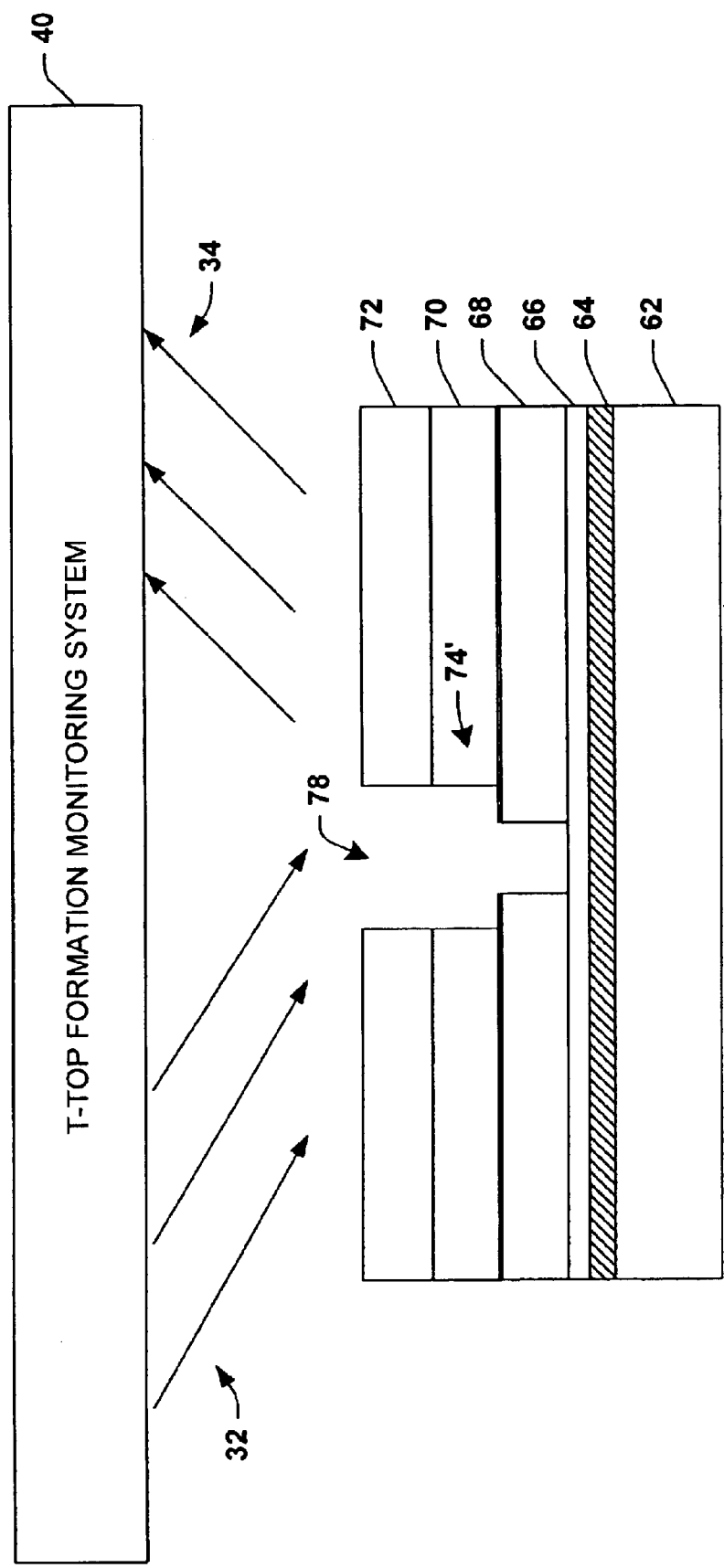
FIG. 10 is a schematic cross-sectional illustration of the structure of FIG. 9 after undergoing etching to expand the opening in the second sacrificial layer and to extend the opening through the first sacrificial layer in accordance with one aspect of the present invention.

Another etching 120 (e.g., anisotropic reactive ion etching (RIE)) (FIG. 9) is performed to extend the opening 74' into the first sacrificial layer 68 and expand the opening 74' at the second sacrificial layer 70 (FIG. 10). Any suitable etching 120 may be used to etch the first and second sacrificial layers 68 and 70, respectively. For example, the first sacrificial layer 68 and the second sacrificial layer 70 at the opening 76 are anisotropically etched with a plasma gas(es), herein carbon tetrafloride ($CF_4$) containing fluorine ions, in a commercially available etcher, such as a parallel plate RIE apparatus or, alternatively, an electron cyclotron resonance (ECR) plasma reactor to thereby extend the opening 74' in the first sacrificial layer 68 and expand the opening 74' at the second sacrificial layer 70. Preferably, a selective etching is used to etch the material of the first and second sacrificial layers 68 and 70 at a relatively greater rate as compared to the rate of the material of the patterned photoresist 72 and an etching that etches the first and second sacrificial layers 68 and 70 at a similar rate to form a T-shaped opening 78. As discussed in association with FIGS. 1 and 2, a light may be directed at the openings 74' and 76 during the etching 120. Light reflecting from the openings 74' and 76 and/or one or more other layers, features and/or openings, for example, can be collected and analyzed to generate a signature associated with the openings 74' and 76. The generated signature can be compared to one or more stored signatures to determine whether to continue, adapt or stop the etching 120. Similarly, a light may be directed at the opening 78. Light reflecting from the opening 78 and/or one or more other layers, features and/or openings, for example, can be collected and analyzed to generate a signature associated with the opening 78. The generated signature can be compared to one or more stored signatures to determine whether to continue, adapt or stop the etching of the opening 78.

Figure 11:
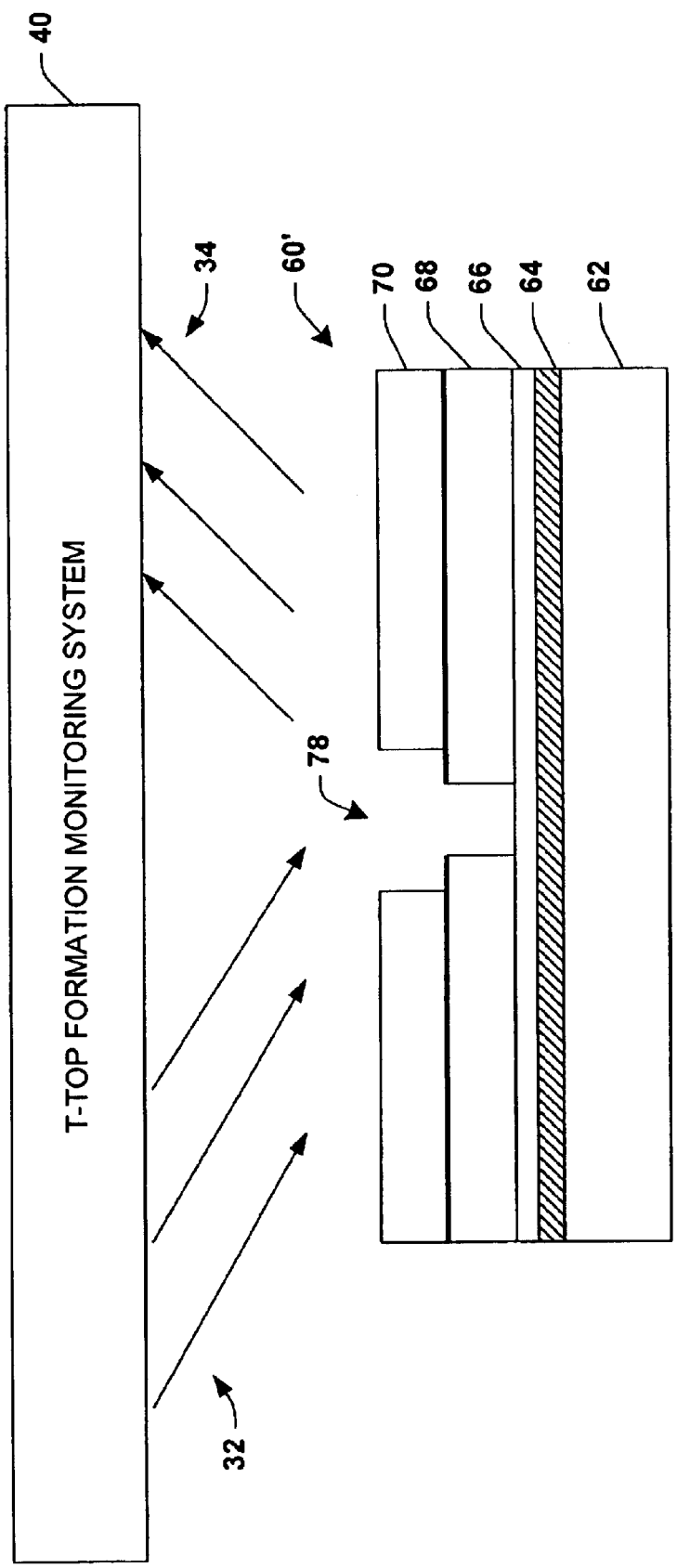
FIG. 11 is a schematic cross-sectional illustration of the structure of FIG. 10 after the photoresist layer has been stripped in accordance with one aspect of the present invention.
Figure 12:
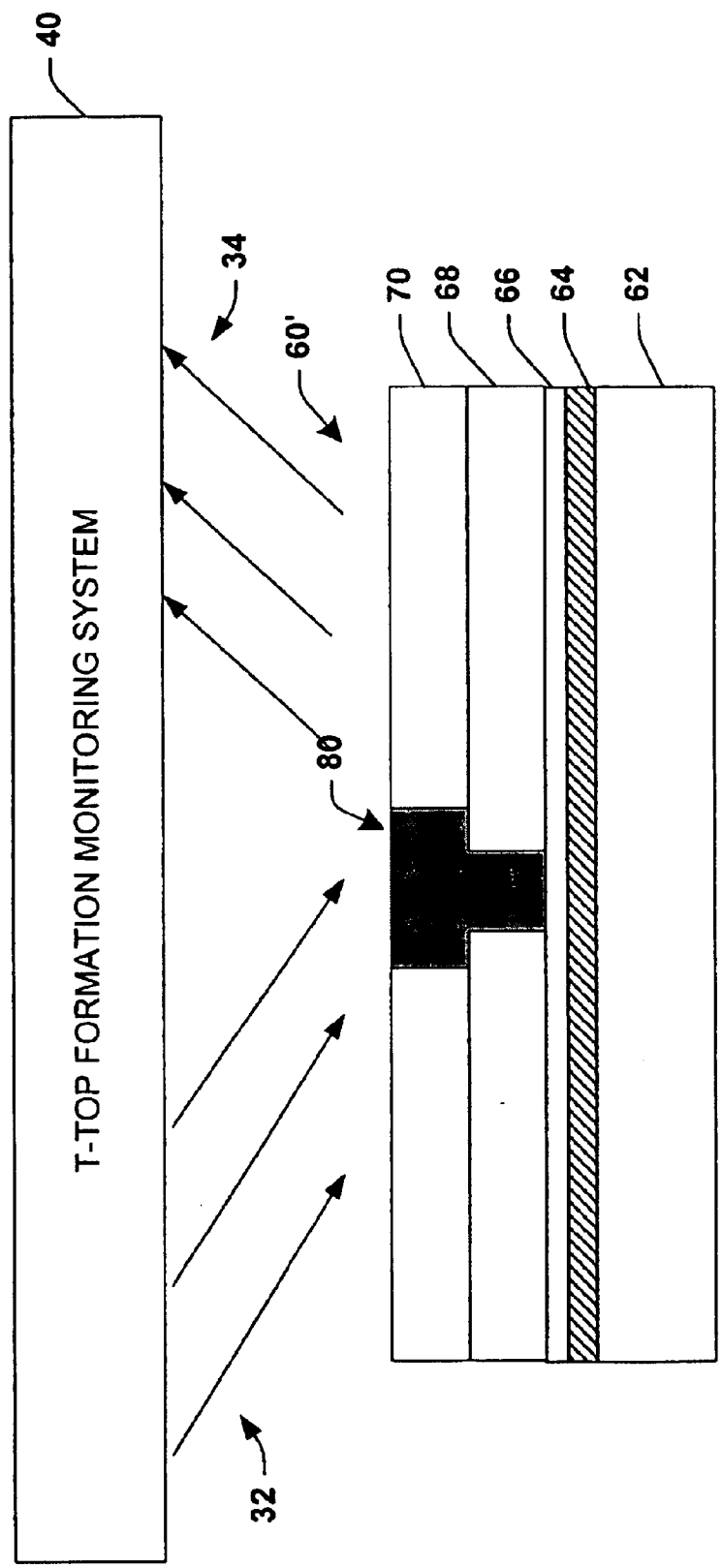
FIG. 12 is a schematic cross-sectional illustration of the structure of FIG. 11 after a deposition has occurred in accordance with one aspect of the present invention.
Figure 13:
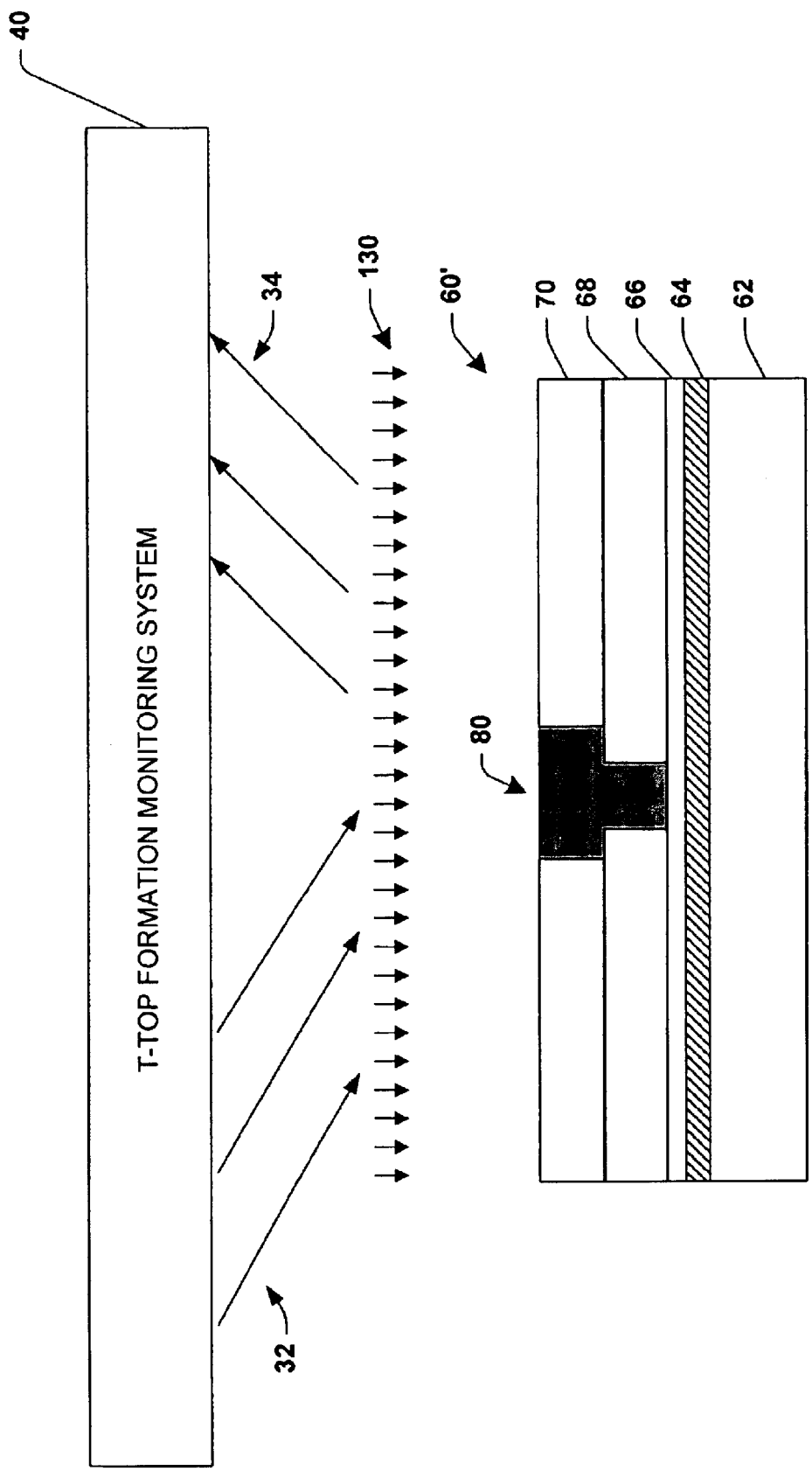
FIG. 13 is a schematic cross-sectional illustration of the structure of FIG. 12 undergoing stripping in accordance with one aspect of the present invention.

FIG. 11 illustrates a partially complete structure 60' after stripping (e.g., ashing in an $O_2$ plasma) is substantially complete for removing the remaining portions of the photoresist layer 72. Next, a damascene fill or deposition is performed on the structure 60' (FIG. 12) to form a T-gate structure 80 in the structure 60'. The T-gate structure 80 can be comprised, for example, of polysilicon, amorphous silicon, germanium, metals or the like. If the T-gate structure 80 is comprised of polysilicon, a contact layer may be formed using any suitable technique including chemical vapor deposition (CVD) techniques (such as low pressure chemical vapor deposition (LPCVD) or plasma enhanced chemical vapor deposition (PECVD). If the T-gate structure 80 is comprised of amorphous silicon or germanium, standard deposition techniques may be employed. If the contact layer is comprised of a metal, standard sputtering techniques may be employed. After formation of the contact layer, the contact layer is polished down to the underlying sacrificial layer to form the T-gate structure 80.

Figure 14:
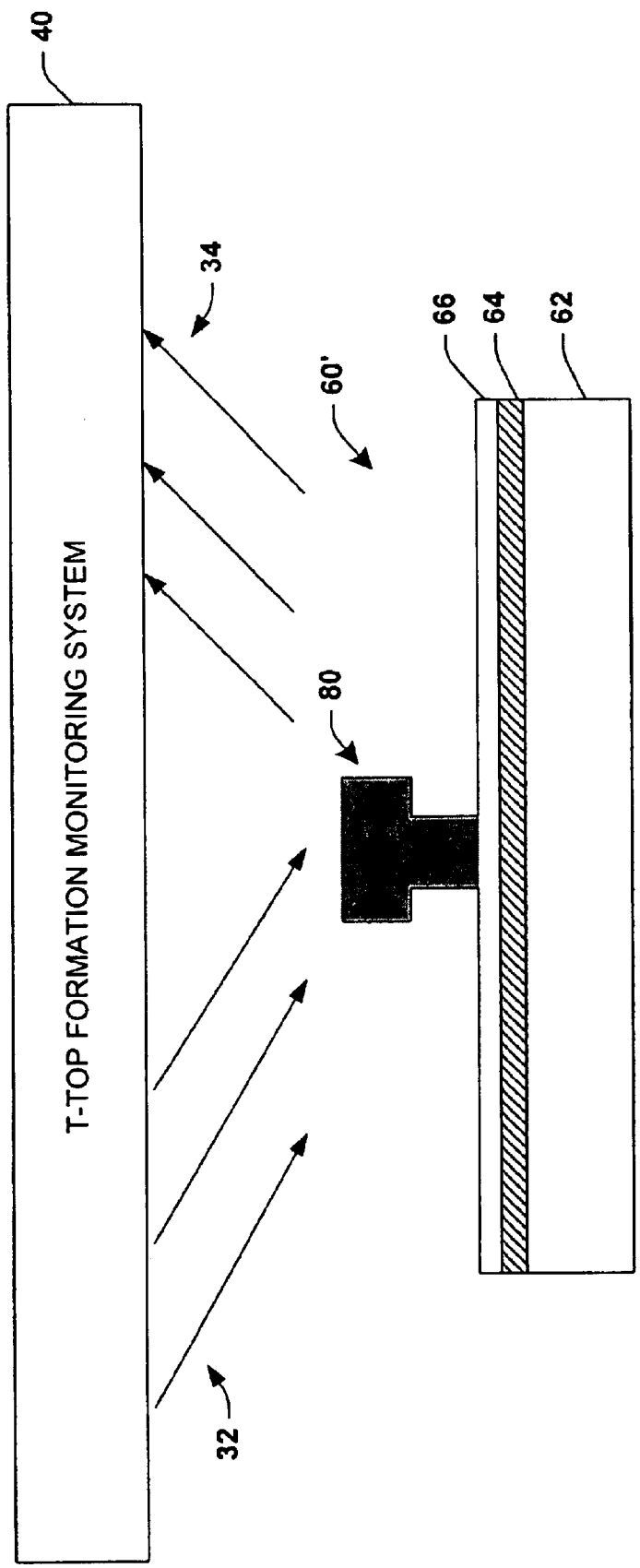
FIG. 14 is a schematic cross-sectional illustration of the structure of FIG. 13 after undergoing stripping in accordance with one aspect of the present invention.

A stripping 130 (FIG. 13) is then performed to remove the first and second sacrificial layers 68 and 70, respectively, to form the structure 60', as illustrated in FIG. 14. The stripping 130 may be an anisotropic gaseous stripping process.

Referring now to FIG. 15–17, another aspect of the present invention is shown. In FIG. 15, a chuck 28 is shown in perspective supporting a wafer 22 whereupon one or more T-gates 100 may be located. The wafer 22 may be divided into a grid pattern as shown in FIG. 16. Each grid block (XY) of the grid pattern corresponds to a particular portion of the wafer 22, and each grid block has one or more features associated with that grid block. Each portion is monitored individually for etching, and each portion is controlled individually for etching. The dimensions of the T-gates 100 can be monitored and determined more precisely to facilitate optimizing T-gate formation.

In FIG. 16, one or more T-gates 100 in the respective portions of the wafer 22 ($X_1Y_1$ ... $X_{12}, Y_{12}$) are being monitored for feature profiles produced during etching using reflected, and/or passed through light, the analysis and monitoring system 40 and the processor 44. The feature profile measurements produced during etching for each T-gate 100 are shown. As can be seen, the feature profile measurement at coordinate $X_7Y_6$ is substantially higher than the feature profile measurement of the other portions XY. It is to be appreciated that the wafer 22 may be partitioned into any suitable number of portions and any suitable number of T-gates 100 may be employed.

FIG. 17 is a representative table of feature profile measurements taken for the various grid blocks that have been correlated with acceptable feature profile values for the portions of the wafer 22 mapped by the respective grid blocks. As can be seen, all the grid blocks, except grid block $X_7Y_6$, have feature profile measurements corresponding to an acceptable feature profile table value ($T_A$) (e.g., are within an expected range of feature profile measurements), while grid block $X_7Y_6$ has an undesired feature profile table value ($T_U$). Thus, the processor 44 and/or analysis and monitoring system 40 have determined a nearly exact location of irregular T-top gate dimensions at the portion of the wafer 22 mapped by grid block $X_7Y_6$. Accordingly, the processor 44 and/or analysis and monitoring system 40 can provide this information to the T-gate fabrication process to facilitate optimization of the T-top gate formation.

Figure 18:
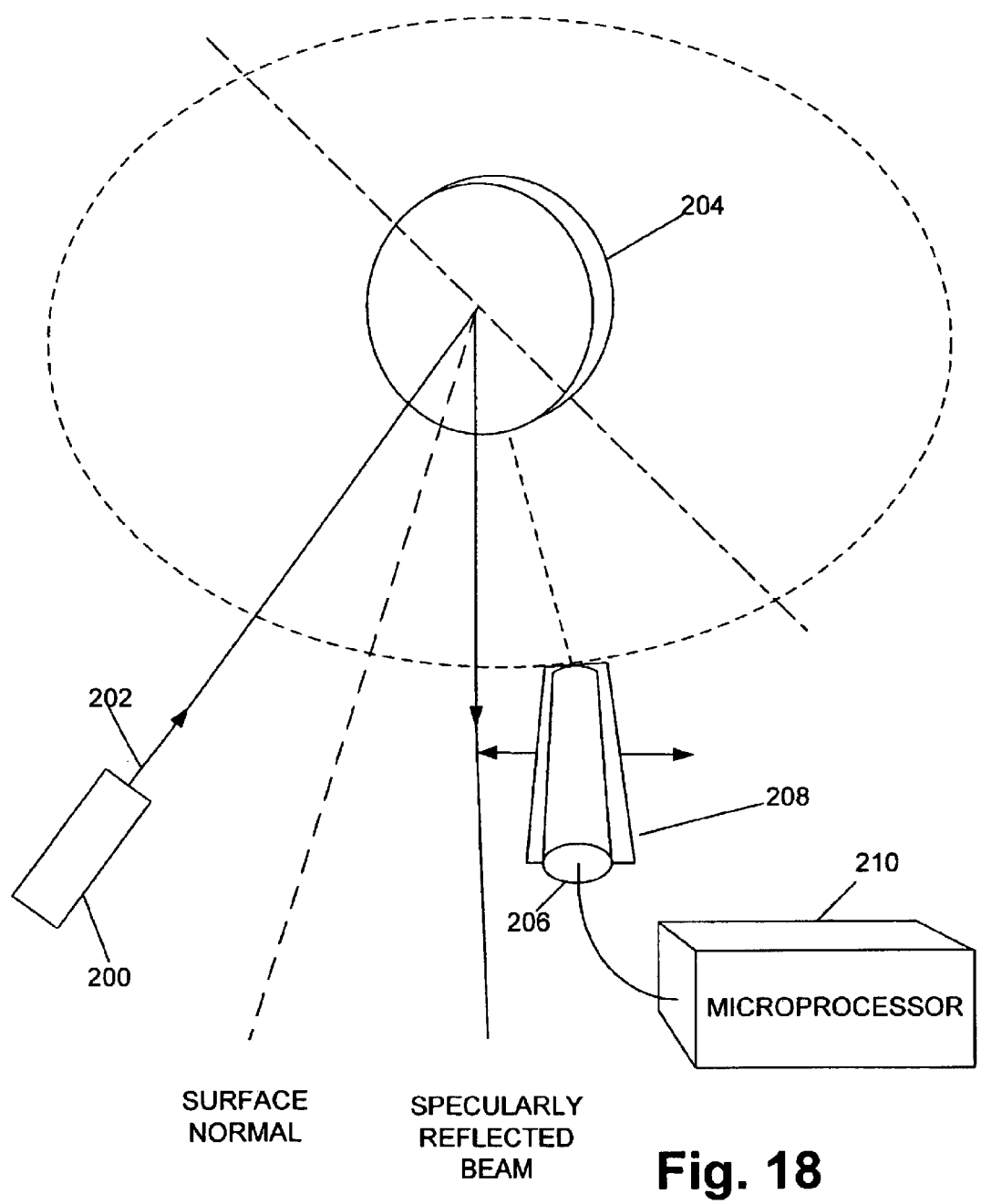
FIG. 18 illustrates an exemplary scatterometry system collecting reflected light.

FIG. 18 illustrates an exemplary scatterometry system collecting reflected light. Light from a laser 200 is brought to focus in any suitable well-known manner to form a beam 202. A sample, such as a wafer 204, is placed in the path of the beam 202 and a photo detector or photo multiplier 206 of any suitable well-known construction. Different detector methods may be employed to determine the scattered power. To obtain a grating pitch, the photo detector or photo multiplier 206 may be mounted on a rotation stage 208 of any suitable well-known design. A microprocessor 210, of any suitable well-known design, may be used to process detector readouts, including, but not limited to, angular locations of different diffracted orders leading to diffraction grating pitches being calculated. Thus, light reflected from the sample 204 may be accurately measured.

Figure 19:
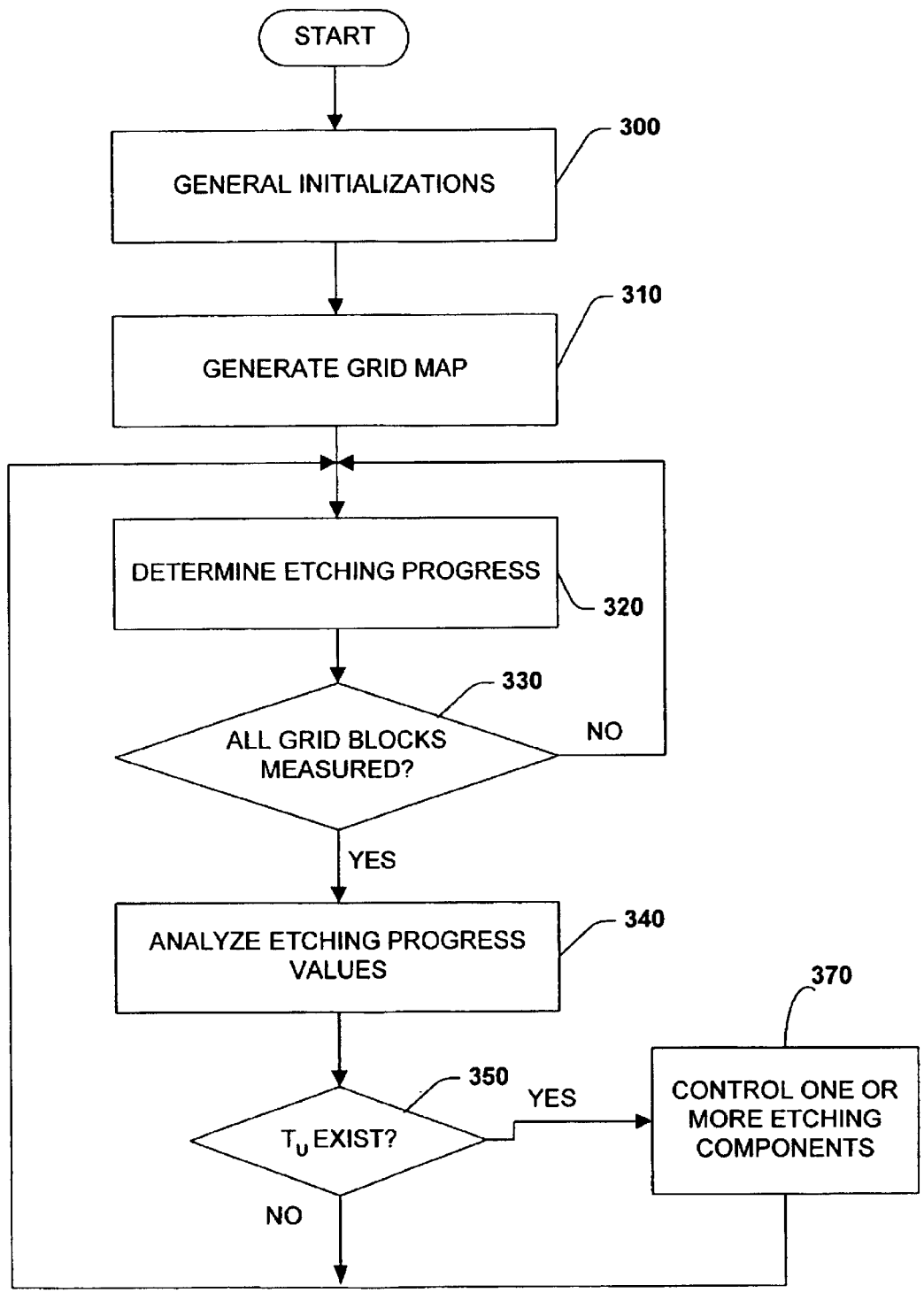
FIG. 19 is a flow diagram illustrating one specific methodology for carrying out the present invention.

In view of the exemplary systems shown and described above, methodologies that may be implemented in accordance with the present invention, will be better appreciated with reference to the flow diagram of FIG. 19. While for purposes of simplicity of explanation, the methodology of FIG. 19 is shown and described as a series of blocks, it is to be understood and appreciated that the present invention is not limited by the order of the blocks, as some blocks may, in accordance with the present invention, occur in different orders and/or concurrently with other blocks from that shown and described herein. Moreover, not all illustrated blocks may be required to implement a methodology in accordance with the present invention.

FIG. 19 is a flow diagram illustrating one particular methodology for carrying out the present invention. At 300, general initializations are performed. The general initializations can include, but are not limited to, allocating memory, establishing pointers, establishing data communications, acquiring resources, setting variables and displaying process activity. At 310, a grid map of a plurality of grid blocks "XY" is created. At 320, feature profile determinations are made with respect to the various wafer portions mapped by the respective grid blocks XY. At 330, a determination is made concerning whether all grid block measurements have been taken. If the determination at 330 is NO, then processing returns to 320. If the determination at 330 is YES, then at 340, determined feature profile values are analyzed and compared against acceptable feature profiles for the respective portions of a wafer.

At 350, a determination is made concerning whether any feature profile values are not acceptable. If all etching values are acceptable, the iteration of the present methodology concludes and processing continues at 320 with another iteration. If unacceptable feature profile values are found, processing proceeds to 370 where the unacceptable feature profile values are analyzed. After the analyses, relevant etching components corresponding to grid blocks with unacceptable feature profile values are controlled to regulate the etching of the respective wafer portions to facilitate achieving desired feature profiles. The present iteration is then ended and the process returns to 320 to perform another iteration.

Scatterometry is a technique for extracting information about a surface upon which an incident light has been directed. Information concerning properties including, but not limited to, dishing, erosion, profile, chemical composition, thickness of thin films and critical dimensions of features present on a surface such as a wafer can be extracted. The information can be extracted by comparing the phase and/or intensity of the light directed onto the surface with phase and/or intensity signals of a complex reflected and/or diffracted light resulting from the incident light reflecting from and/or diffracting through the surface upon which the incident light was directed. The intensity and/or the phase of the reflected and/or diffracted light will change based on properties of the surface upon which the light is directed. Such properties include, but are not limited to, the chemical properties of the surface, the planarity of the surface, features on the surface, voids in the surface, and the number and/or type of layers beneath the surface.

Different combinations of the above-mentioned properties will have different effects on the phase and/or intensity of the incident light resulting in substantially unique intensity/phase signatures in the complex reflected and/or diffracted light. Thus, by examining a signal (signature) library of intensity/phase signatures, a determination can be made concerning the properties of the surface. Such substantially unique phase/intensity signatures are produced by light reflected from and/or refracted by different surfaces due, at least in part, to the complex index of refraction of the surface onto which the light is directed. The complex index of refraction (N) can be computed by examining the index of refraction (n) of the surface and an extinction coefficient (k). One such computation of the complex index of refraction can be described by the equation:

$$N = n - jk$$

where j is an imaginary number.

The signal (signature) library can be constructed from observed intensity/phase signatures and/or signatures generated by modeling and simulation. By way of illustration, when exposed to a first incident light of known intensity, wavelength and phase, a first feature on a wafer can generate a first phase/intensity signature. Similarly, when exposed to the first incident light of known intensity, wavelength and phase, a second feature on a wafer can generate a second phase/intensity signature. For example, a line of a first width may generate a first signature while a line of a second width may generate a second signature. Observed signatures can be combined with simulated and modeled signatures to form the signal (signature) library. Simulation and modeling can be employed to produce signatures against which measured phase/intensity signatures can be matched. In one exemplary aspect of the present invention, simulation, modeling and observed signatures are stored in a signal (signature) library containing over three hundred thousand phase/intensity signatures. Thus, when the phase/intensity signals are received from scatterometry detecting components, the phase/intensity signals can be pattern matched, for example, to the library of signals to determine whether the signals correspond to a stored signature.

Figure 20:
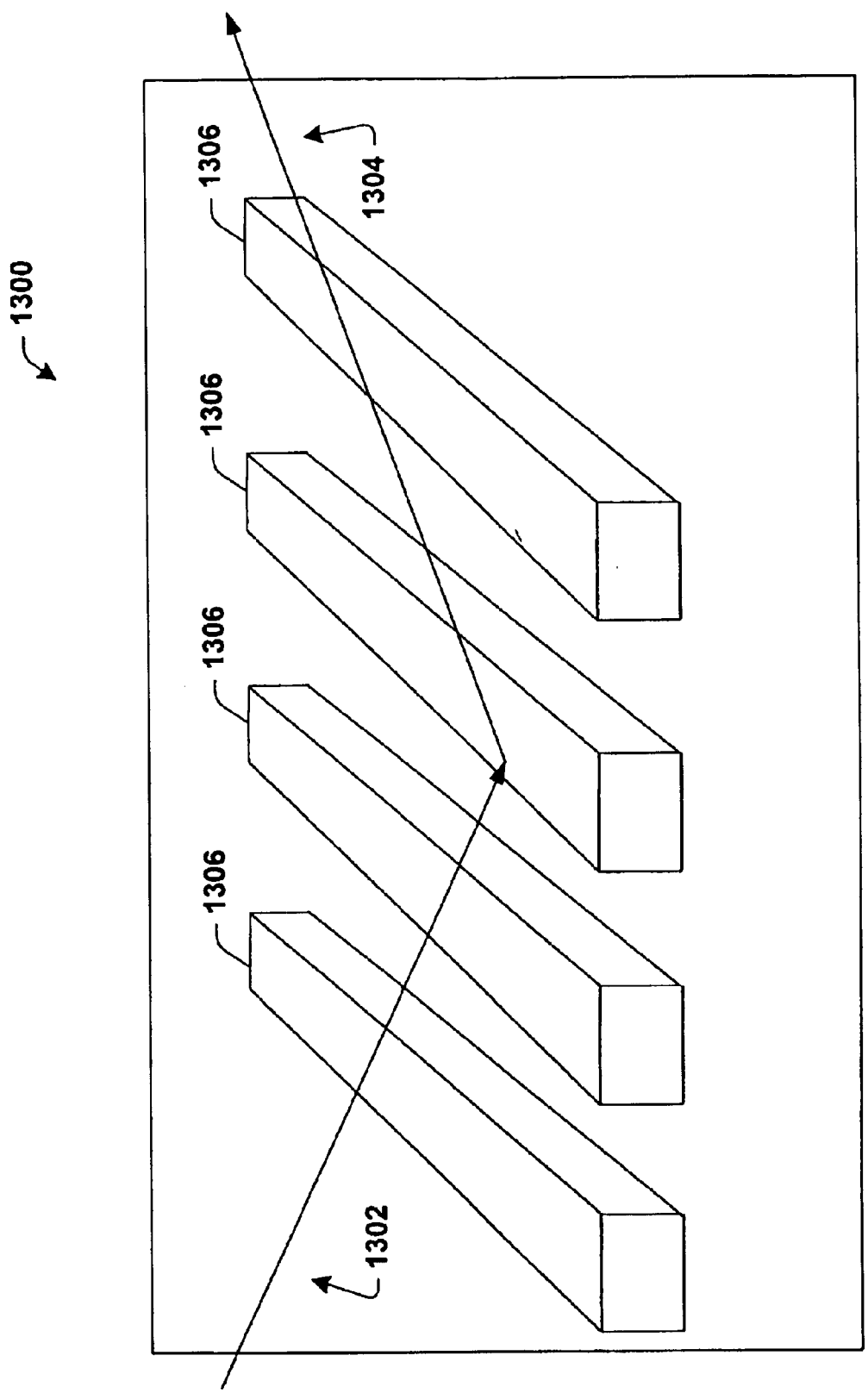
FIG. 20 is a simplified perspective view of an incident light reflecting off a surface, in accordance with an aspect of the present invention.

To illustrate the principles described above, reference is now made to FIGS. 20 through 24. Referring initially to FIG. 20, an incident light 1302 is directed at a surface 1300, upon which one or more features 1306 may exist. The incident light 1302 is reflected as reflected light 1304. The properties of the surface 1300, including but not limited to, thickness, uniformity, planarity, chemical composition and the presence of features, can affect the reflected light 1304. The features 1306 are raised upon the surface 1300. The phase and intensity of the reflected light 1304 can be measured and plotted, as shown, for example, in FIG. 24. Such plots can be employed to compare measured signals with signatures stored in a signature library using techniques like pattern matching, for example.

Figure 21:
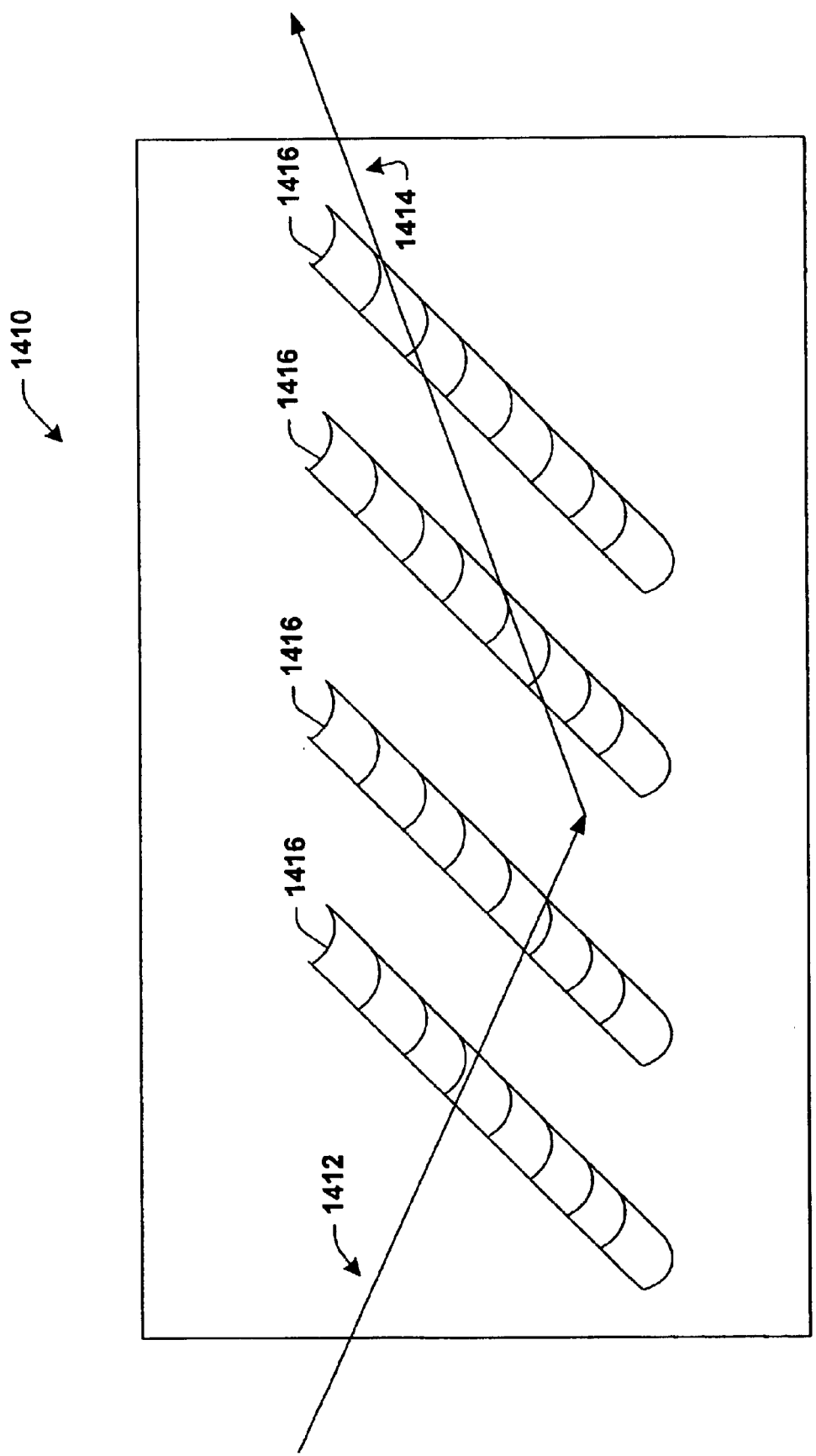
FIG. 21 is a simplified perspective view of an incident light reflecting off a surface, in accordance with an aspect of the present invention.

Referring now to FIG. 21, an incident light 1412 is directed onto a surface 1410 upon which one or more depressions 1416 appear. The incident light 1412 is reflected as reflected light 1414. Like the one or more features 1306 (FIG. 20) may affect an incident beam, so too may the one or more depressions 1416 affect an incident beam. Thus, it is to be appreciated that scatterometry can be employed to measure features appearing on a surface, features appearing in a surface, and properties of a surface itself, regardless of features.

Figure 22:
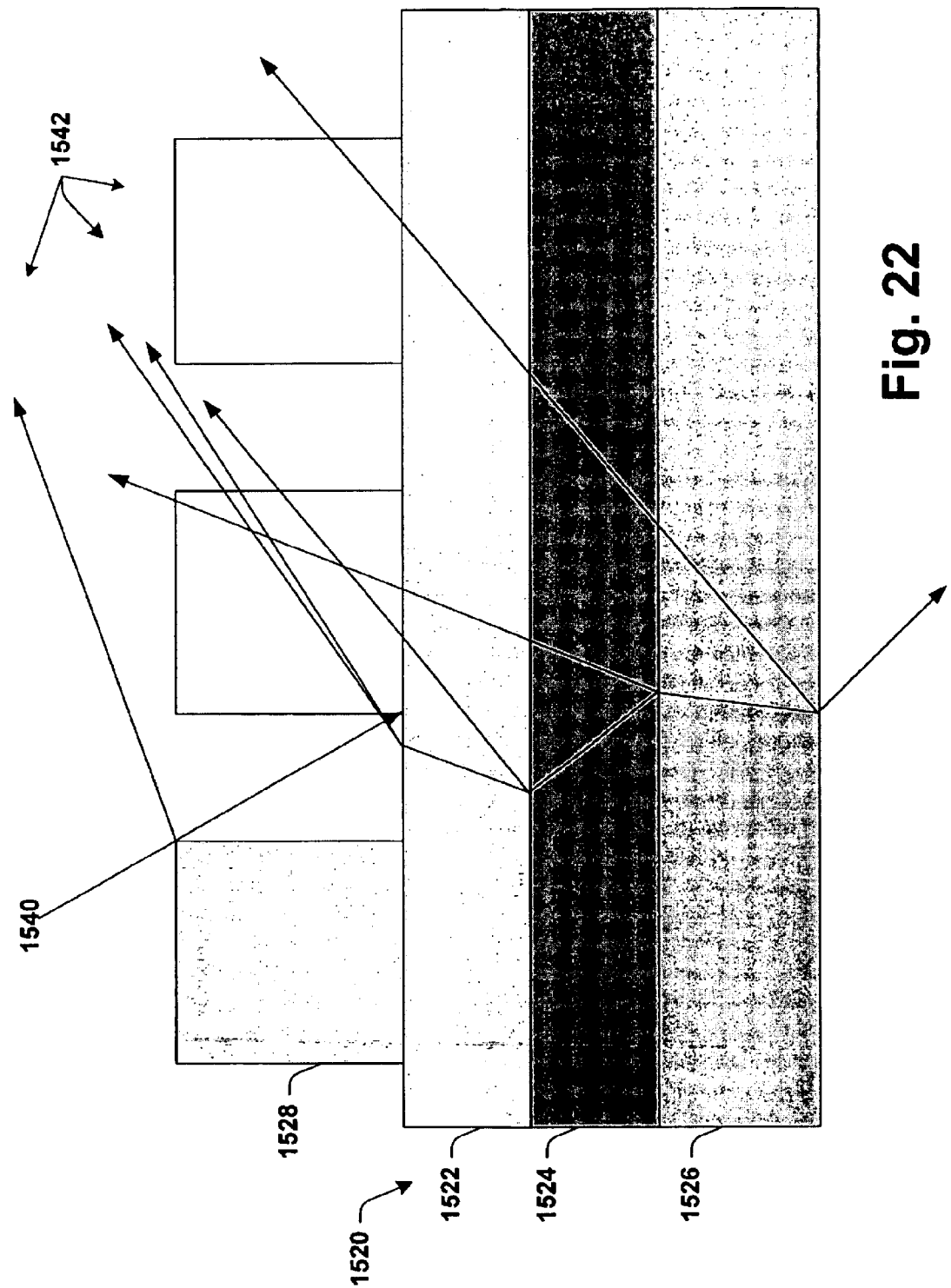
FIG. 22 illustrates a complex reflected and refracted light produced when an incident light is directed onto a surface, in accordance with an aspect of the present invention.

Turning now to FIG. 22, complex reflections and refractions of an incident light 1540 are illustrated. The reflection and refraction of the incident light 1540 can be affected by factors including, but not limited to, the presence of one or more features 1528, and the composition of the substrate 1520 upon which the features 1528 reside. For example, properties of the substrate 1520 including, but not limited to the thickness of a layer 1522, the chemical composition of the layer 1522, the opacity and/or reflectivity of the layer 1522, the thickness of a layer 1524, the chemical composition of the layer 1524, the opacity and/or reflectivity of the layer 1524, the thickness of a layer 1526, the chemical composition of the layer 1526, and the opacity and/or reflectivity of the layer 1526 can affect the reflection and/or refraction of the incident light 1540. Thus, a complex reflected and/or refracted light 1542 may result from the incident light 1540 interacting with the features 1528, and/or the layers 1522, 1524 and 1526. Although three layers 1522, 1524 and 1526 are illustrated, it is to be appreciated that a substrate can be formed of a greater or lesser number of such layers.

Figure 23:
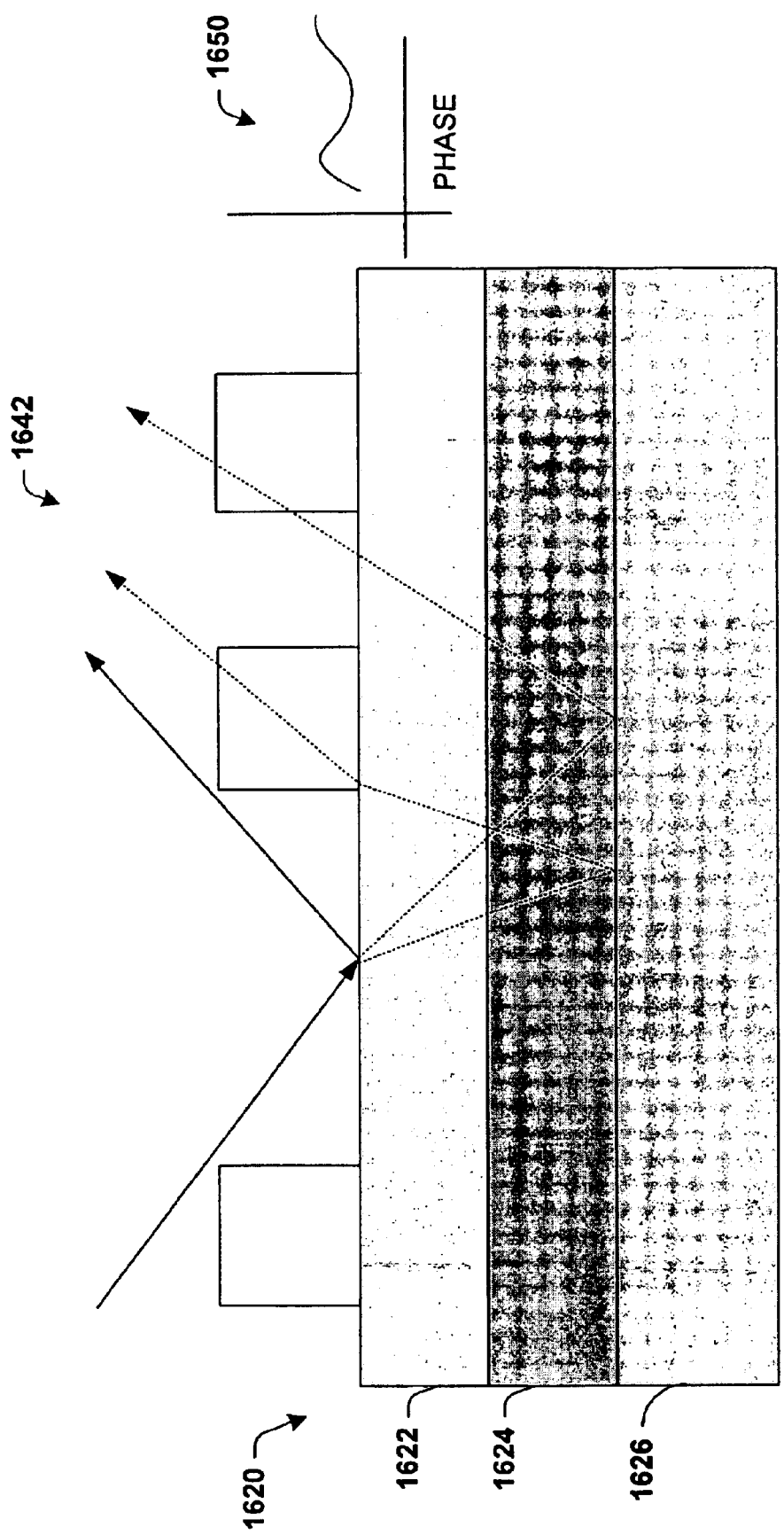
FIG. 23 illustrates a complex reflected and refracted light produced when an incident light is directed onto a surface, in accordance with an aspect of the present invention.
Figure 24:
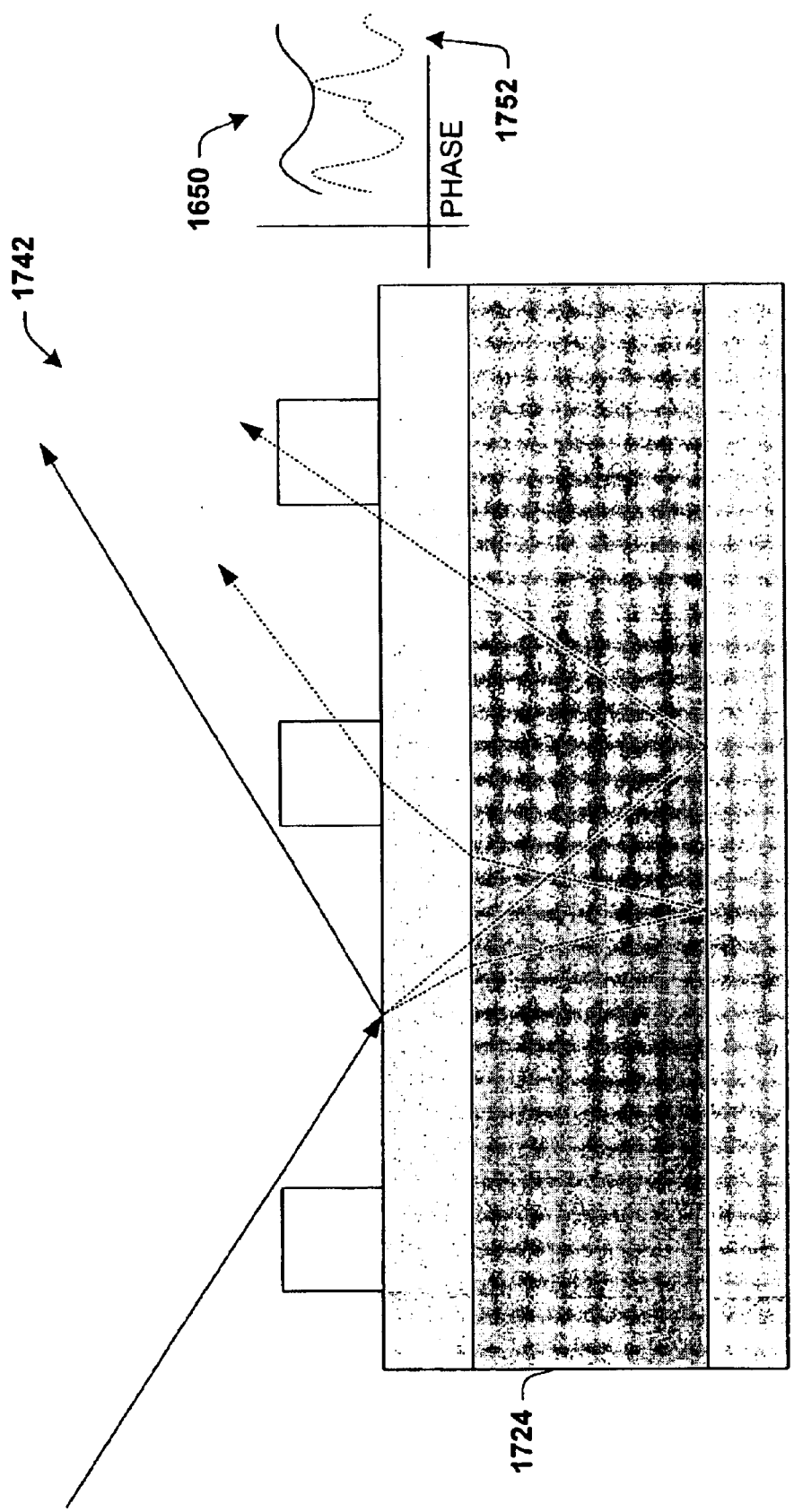
FIG. 24 illustrates a complex reflected and refracted light produced when an incident light is directed onto a surface, in accordance with an aspect of the present invention.
Figure 25:
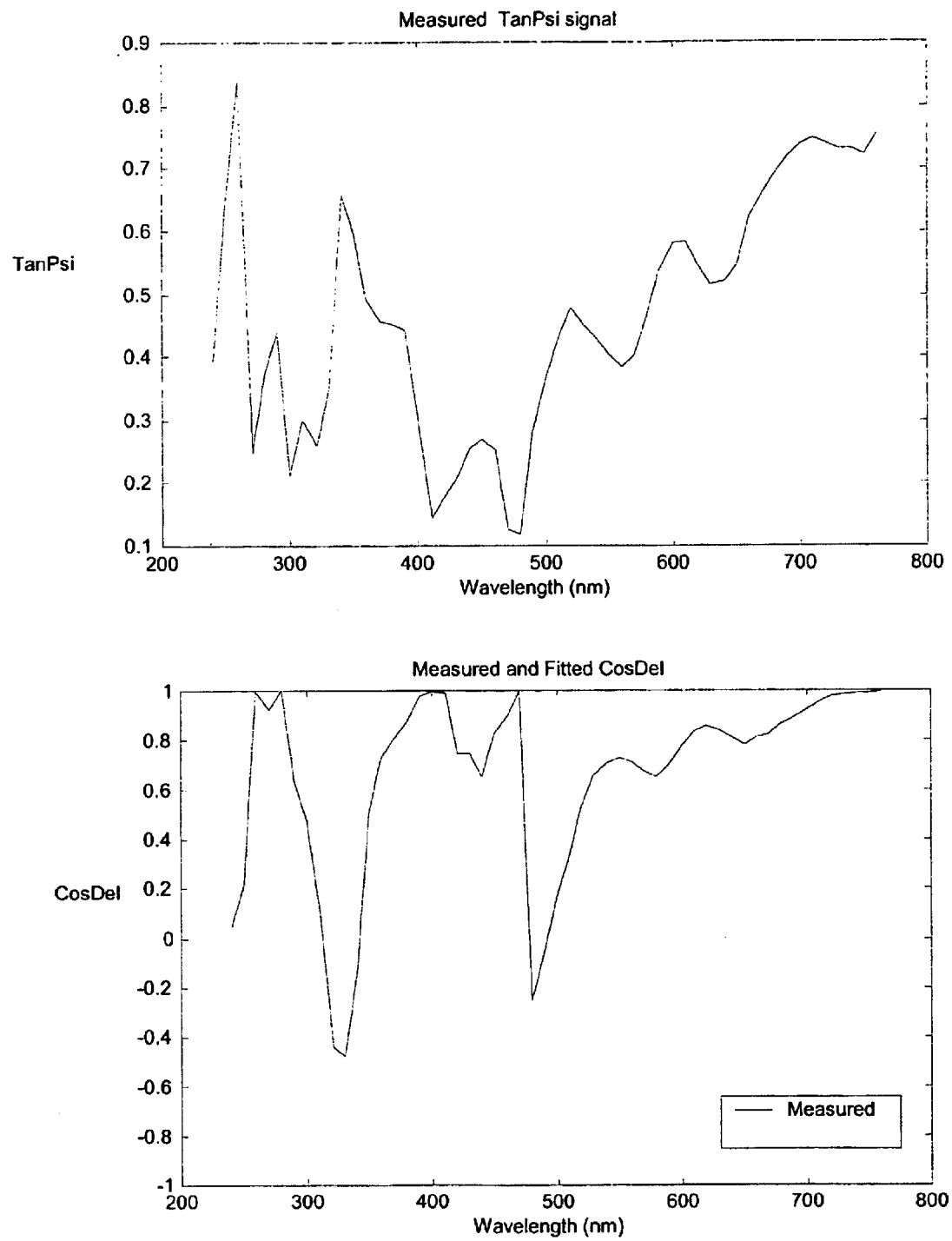
FIG. 25 illustrates phase and intensity signals recorded from a complex reflected and refracted light produced when an incident light is directed onto a surface, in accordance with an aspect of the present invention.

Turning now to FIG. 23, one of the properties from FIG. 24 is illustrated in greater detail. The substrate 1620 can be formed of one or more layers 1622, 1624 and 1626. The phase 1650 of the reflected and/or refracted light 1642 can depend, at least in part, on the thickness of a layer, for example, the layer 1624. Thus, in FIG. 24, the phase 1752 of a reflected light 1742 differs from the phase 1650 due, at least in part, to the different thickness of the layer 1724 in FIG. 24 from the thickness of the layer 1624 in FIG. 23.

Thus, scatterometry is a technique that can be employed to extract information about a surface upon which an incident light has been directed. The information can be extracted by analyzing phase and/or intensity signals of a complex reflected and/or diffracted light. The intensity and/or the phase of the reflected and/or diffracted light will change based on properties of the surface upon which the light is directed, resulting in substantially unique signatures that can be analyzed to determine one or more properties of the surface upon which the incident light was directed.

The present invention provides for a system and method for regulating development time. As a result, the present invention facilitates improving development integrity and reliability, which in turn increases quality of image transfer in lithographic processes in accordance with the present invention.

What has been described above includes examples of the present invention. It is, of course, not possible to describe every conceivable combination of components or methodologies for purposes of describing the present invention, but one of ordinary skill in the art may recognize that many further combinations and permutations of the present invention are possible. Accordingly, the present invention is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A method for monitoring T-top gate formation comprising:

providing a wafer structure undergoing a T-top gate fabrication process;

generating a signature associated with the wafer structure during a process step to monitor formation of the T-top gate; and comparing the generated signature to a signature store to determine a state of the T-top gate.

2. The method of claim 1, wherein a scatterometry system is employed to generate the signature associated with the wafer structure.

3. The method of claim 1, wherein generating the signature comprises:

directing a beam of incident light at the wafer structure;

collecting a light reflected from the wafer structure; and transforming the reflected light into the signature.

4. The method of claim 1, wherein the signature corresponds to a particular profile associated with the wafer undergoing T-top gate formation.

5. The method of claim 1, wherein an analysis system compares the generated signature to the signature store to determine the state of the T-top gate.

6. The method of claim 1, further comprising feeding information relating to the state of the T-top gate back into the T-top gate fabrication process to optimize T-top gate formation.

7. An in-line method for determining T-top gate dimensions comprising:

providing a wafer structure having a T-top gate formed thereon;

generating a signature associated with the T-top gate;

comparing the generated signature with a signature store to determine the dimensions of the T-top gate; and adjusting T-top gate process parameters using feedback control.

8. The method of claim 7, wherein a scatterometry system is employed to generate the signature associated with the T-top gate.

9. The method of claim 7, wherein generating the signature comprises:

directing a beam of incident light at the wafer structure;

collecting a light reflected from the wafer structure; and transforming the reflected light into the signature.

10. The method of claim 7, wherein the signature corresponds to a particular profile associated with the wafer undergoing T-top gate formation.

11. The method of claim 7, wherein an analysis system compares the generated signature to the signature store to determine the state of the T-top gate.

12. The method of claim 7, wherein adjusting T-top gate process parameters using feedback control comprises feeding information relating to the state of the T-top gate back into the T-top gate fabrication process to optimize T-top gate formation.

13. The method of claim 7, wherein T-top gate dimensions comprises amount of undercut and effective gate width.

14. The method of claim 7, further comprising generating a schematic cross-section of the T-top gate to determine its profile and dimensions.

15. The method of claim 14, wherein the schematic cross-section of the T-top gate is generated from the light reflected from the wafer structure.

16. An in-line method for determining T-top gate dimensions comprising:

providing a wafer structure having a T-top gate formed thereon;

directing an incident beam of light at the T-top gate;

collecting the reflected light associated with the T-top gate;

generating a signature associated with the T-top gate using the reflected light;

comparing the generated signature with a signature store to determine the dimensions of the T-top gate; and adjusting T-top gate process parameters using feedback control.

17. The method of claim 16, wherein a scatterometry system is employed to generate the signature associated with the T-top gate.

18. The method of claim 16, wherein the signature corresponds to a particular profile associated with the wafer undergoing T-top gate formation.

19. The method of claim 16, wherein an analysis system compares the generated signature to the signature store to determine the state of the T-top gate.

20. The method of claim 16, wherein adjusting T-top gate process parameters using feedback control comprises feeding information relating to the state of the T-top gate back into the T-top gate fabrication process to optimize T-top gate formation.

21. The method of claim 16, wherein T-top gate dimensions comprises amount of undercut and effective gate width.

22. The method of claim 16, further comprising generating a schematic cross-section of the T-top gate to determine its profile and dimensions.

23. The method of claim 22, wherein the schematic cross-section of the T-top gate is generated from the light reflected from the wafer structure.

24. An in-line system for monitoring T-top gate formation comprising:

a wafer structure undergoing a T-top gate formation process;

a T-top gate formation monitoring system for generating a signature associated with wafer surface dimensions during a process step; and a signature store coupled to the monitoring system, wherein the generated signature is compared to the signature store to determine a state of the T-top gate.

25. The system of claim 24, further comprising a scatterometry system that monitors the T-top gate formation.

26. The system of claim 24, wherein the T-top gate formation signature store comprises known signatures of wafer structures as they appear during the T-top gate formation process.

27. The system of claim 24, wherein the signature corresponds to a particular profile associated with the wafer undergoing T-top gate formation.

28. The system of claim 24, wherein wafer surface dimensions comprise amount of undercut and effective gate width.

29. The system of claim 24, further comprising a feedback control system operatively coupled to the T-top gate formation monitoring system.

30. An in-line system for determining T-top gate dimensions comprising:

a wafer structure undergoing a T-top gate formation process;

a scatterometry system that directs light to the wafer structure and collects light therefrom, as part of the formation process;

a signature store comprising known signatures associated with T-top gate formation;

a T-top gate formation analysis system coupled to the scatterometry system and to the signature store for determining the T-top gate dimensions; and a feedback control system coupled to the T-top gate formation analysis system for optimizing T-top gate formation.

31. The system of claim 30, wherein the T-top gate formation signature store comprises known signatures of wafer structures as they appear during the T-top gate formation process.

32. The system of claim 30, wherein the signature corresponds to a particular profile associated with the wafer structure undergoing T-top gate formation.

33. The system of claim 30, wherein the T-top gate dimensions comprise amount of undercut and effective gate width.

34. An in-line system for determining T-top gate dimensions comprising:

means for providing a wafer structure having a T-top gate formed thereon;

means for generating a signature associated with the T-top gate;

means for comparing the generated signature with a signature store to determine the dimensions of the T-top gate; and means for adjusting T-top gate process parameters using feedback control.

* * * * *

UNITED STATES PATENT AND TRADEMARK OFFICE
CERTIFICATE OF CORRECTION

PATENT NO. : 6,778,268 B1
DATED : August 17, 2004
INVENTOR(S) : Bhanwar Singh et al.

It is certified that error appears in the above-identified patent and that said Letters Patent is hereby corrected as shown below:

Title page,
Item [73], Assignee, replace "Advanced Micro Devices, Sinc." with -- Advanced Micro Devices, Inc. --

Column 3,
Line 27, remove the word "ret"

Signed and Sealed this

Fourteenth Day of December, 2004

JON W. DUDAS
*Director of the United States Patent and Trademark Office*